US010149599B2

(12) United States Patent
Ito

(10) Patent No.: US 10,149,599 B2
(45) Date of Patent: Dec. 11, 2018

(54) PROCESSING APPARATUS

(71) Applicant: OLYMPUS CORPORATION, Tokyo (JP)

(72) Inventor: Ryosuke Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/671,763

(22) Filed: Aug. 8, 2017

(65) Prior Publication Data

US 2017/0332880 A1    Nov. 23, 2017

Related U.S. Application Data

(63) Continuation of application No. PCT/JP2015/055002, filed on Feb. 23, 2015.

(51) Int. Cl.
*G01B 9/02* (2006.01)
*A61B 1/00* (2006.01)
(Continued)

(52) U.S. Cl.
CPC ........... *A61B 1/00009* (2013.01); *A61B 1/05* (2013.01); *A61B 1/0684* (2013.01); *G01N 21/27* (2013.01);
(Continued)

(58) Field of Classification Search
CPC ..... A61B 1/00009; A61B 1/05; A61B 1/0684; G01N 21/27; G01N 21/47; G01N 21/4795;
(Continued)

(56) References Cited

U.S. PATENT DOCUMENTS 5,807,264 A    9/1998  Paltieli
7,652,772 B2 *  1/2010  Backman .............. G01J 3/02
                                                 356/497
(Continued)

FOREIGN PATENT DOCUMENTS

WO    WO 2009/008745 A2    1/2009
WO    WO 2014/042130 A1    3/2014

OTHER PUBLICATIONS

International Search Report dated Mar. 31, 2015 issued in PCT/JP2015/055002.
(Continued)

*Primary Examiner* — Tarifur R Chowdhury
*Assistant Examiner* — Jonathon Cook
(74) *Attorney, Agent, or Firm* — Scully, Scott, Murphy & Presser, P.C.

(57) ABSTRACT

A processing apparatus includes: a light source unit configured to emit partially coherent light having a coherence length that is equal to or more than inverse of a scattering coefficient of a light scattering body and shorter than half of inverse of a reduced scattering coefficient of the light scattering body; an illumination unit configured to irradiate an illumination area on a surface of the light scattering body, with the partially coherent light emitted from the light source unit; a detection unit configured to detect, in a detection area including the illumination area, a signal of scattered and returned light from the light scattering body; and an interference component extracting unit configured to extract an interference component by excluding a noninterference component from the signal of the scattered and returned light detected by the detection unit.

14 Claims, 44 Drawing Sheets

(51) Int. Cl.
*G01N 21/27* (2006.01)
*G01N 21/47* (2006.01)
*A61B 1/05* (2006.01)
*A61B 1/06* (2006.01)
*G01N 21/45* (2006.01)
*G01N 21/49* (2006.01)

(52) U.S. Cl.
CPC ............. *G01N 21/45* (2013.01); *G01N 21/47* (2013.01); *G01N 21/49* (2013.01); *G01N 2021/479* (2013.01); *G01N 2201/062* (2013.01)

(58) Field of Classification Search
CPC ..... G01N 2021/4709; G01N 2201/062; G01B 9/02007; G01B 9/02009; G01B 9/02034; G01B 9/02035; G01B 9/0207; G01B 9/0209; G01H 9/004
USPC .................................................. 356/477, 479
See application file for complete search history.

(56) References Cited

U.S. PATENT DOCUMENTS

| | | | |
|---|---|---|---|
| 9,226,661 B2 | 1/2016 | Thompson et al. | |
| 9,329,124 B2 | 5/2016 | Ito | |
| 2005/0190372 A1* | 9/2005 | Dogariu | A61B 5/0066 356/479 |
| 2011/0176142 A1* | 7/2011 | Hacker | A61B 3/102 356/479 |
| 2013/0063727 A1* | 3/2013 | Xu | A61B 5/0066 356/479 |

OTHER PUBLICATIONS

Turzhitsky,V., et.al, "Characterization of Light Transport in Scattering Media at Subdiffusion Length Scales with Low-Coherence Enhanced Backscattering," IEEE Journal of Selected Topics in Quantum Electronics, May/Jun. 2010, vol. 16, No. 3, pp. 619-626.
Kim, Y.L., et.al, "Low-coherence enhanced backscattering of light: characteristics and applications for colon cancer screening," Proceedings of SPIE, 2007, vol. 6446, 644606, pp. 1-12.

* cited by examiner

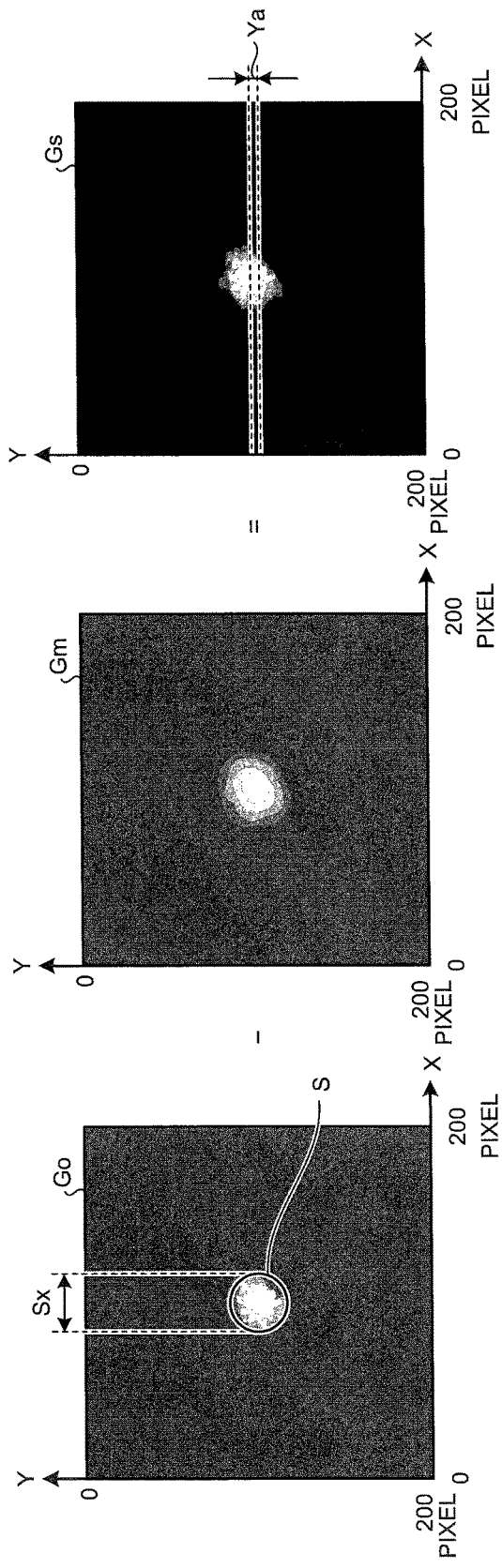

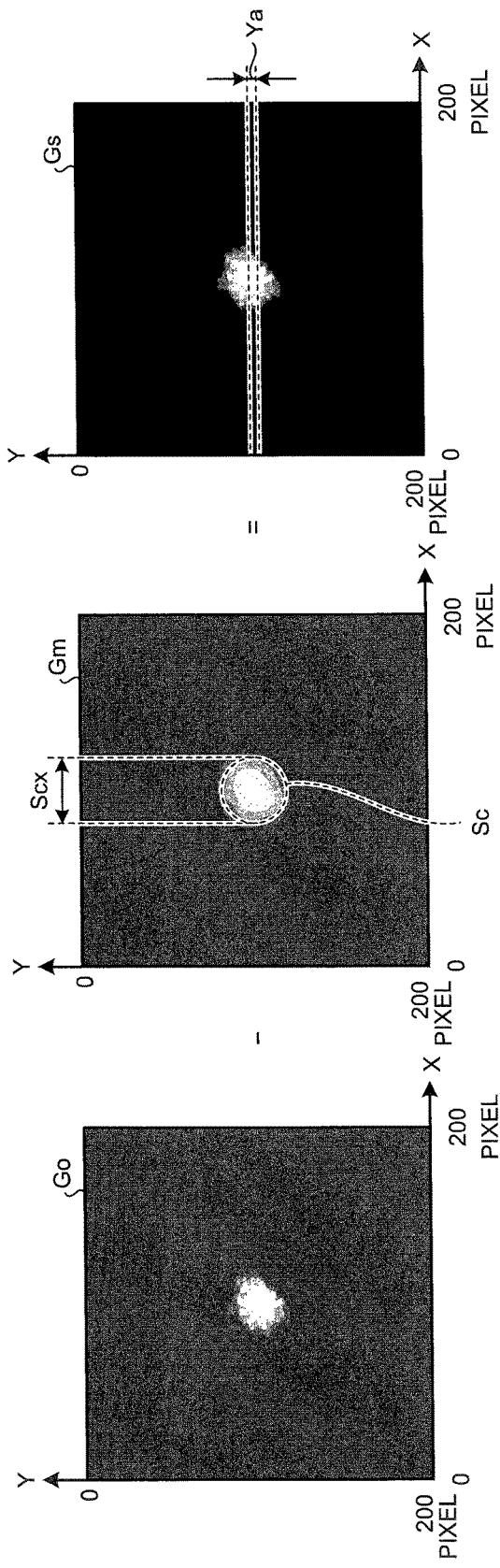

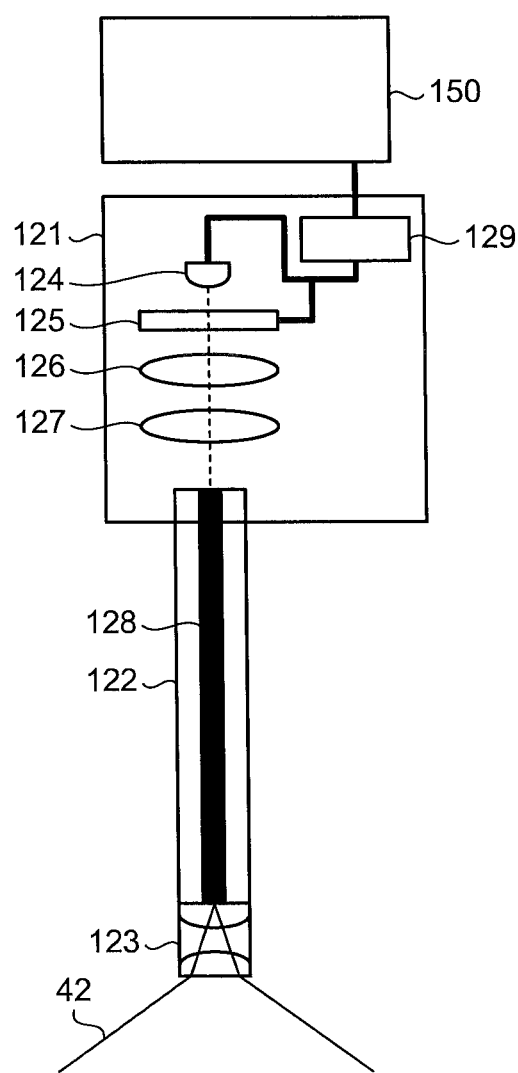

BPF:ON

BPF:OFF
NDF:ON

| | X → | | | |
|---|---|---|---|---|
| Y ↓ | R | $\lambda_3'$ | R | $\lambda_3'$ | ... |
| | $\lambda_4'$ | B | $\lambda_4'$ | B | ... |
| | R | $\lambda_3'$ | R | $\lambda_3'$ | ... |
| | $\lambda_4'$ | B | $\lambda_4'$ | B | ... |
| | ... | ... | ... | ... | ... |

1051c

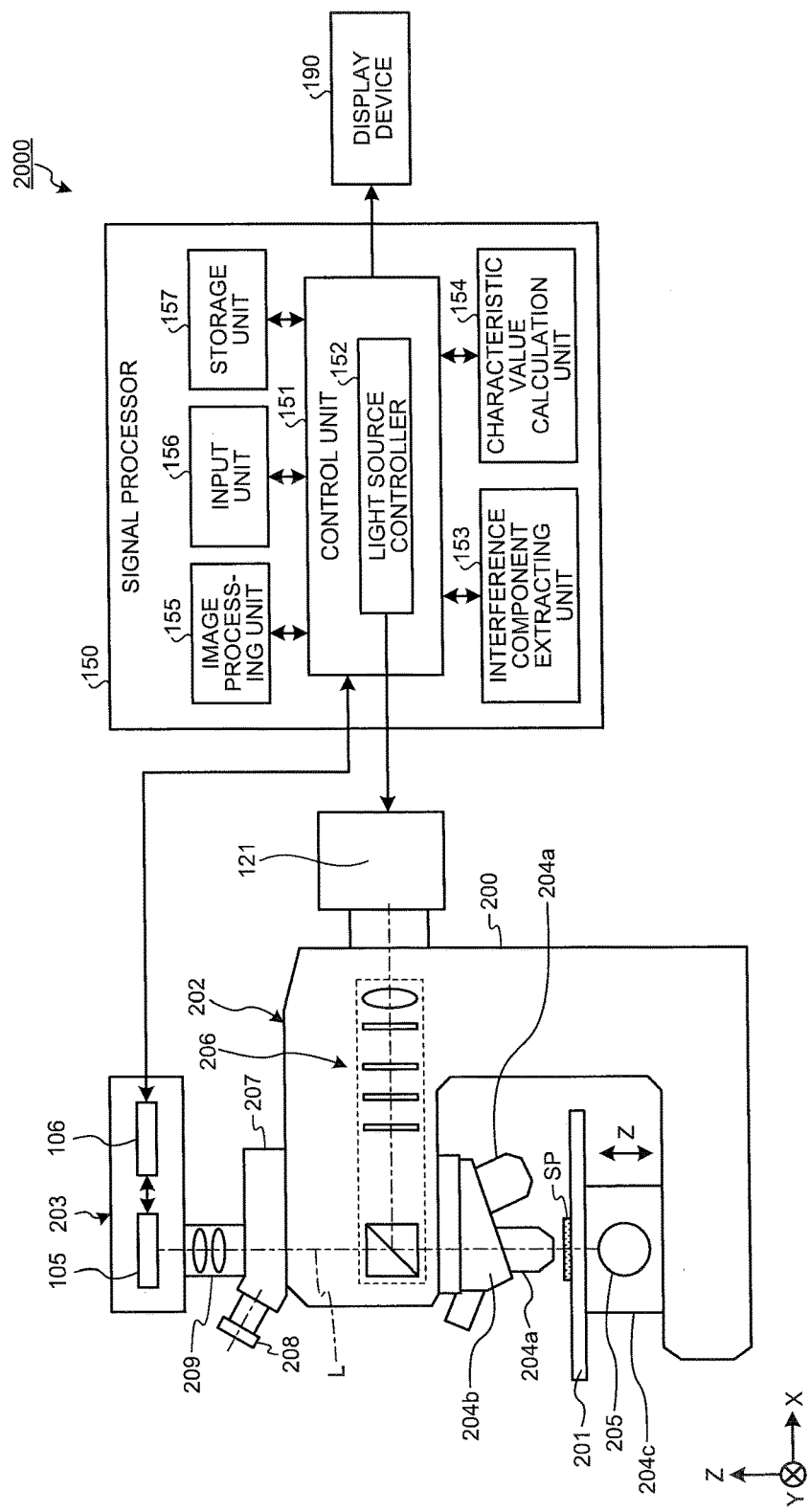

PROCESSING APPARATUS

CROSS REFERENCES TO RELATED APPLICATIONS

This application is a continuation of International Application No. PCT/JP2015/055002, filed on Feb. 23, 2015, the entire contents of which are incorporated herein by reference.

BACKGROUND

1. Technical Field

The disclosure relates to a processing apparatus for irradiating a light scattering body with partially coherent light and extracting an interference component from the light scattered and returned from the light scattering body.

2. Related Art

Conventionally, there have been techniques that acquire dynamic information of a body tissue such as ciliary motion or blood flow by irradiating the body tissue with partially coherent light, detecting returned light which has been back scattered inside the body tissue and returned, and obtaining fluctuations in the interference (laser speckle) signal (refer to U.S. Pat. No. 5,807,264 and WO 2009/008745, for example).

SUMMARY

In some embodiments, a processing apparatus includes: a light source unit configured to emit partially coherent light having a coherence length that is equal to or more than inverse of a scattering coefficient of a light scattering body and shorter than half of inverse of a reduced scattering coefficient of the light scattering body; an illumination unit configured to irradiate an illumination area on a surface of the light scattering body, with the partially coherent light emitted from the light source unit; a detection unit configured to detect, in a detection area including the illumination area, a signal of scattered and returned light from the light scattering body; and an interference component extracting unit configured to extract an interference component by excluding a noninterference component from the signal of the scattered and returned light detected by the detection unit.

In some embodiments, a processing apparatus includes: a light source unit configured to emit partially coherent light having a predefined coherence length for a scattering body of the same kind as a light scattering body, the predefined coherence length being defined to generate an interference component within an area showing an intensity of 10% of a maximum intensity of scattered and returned light from a center point of a focused illumination area on the scattering body, among an intensity distribution of internally scattered and returned light that is formed on a surface of the scattering body when focused illumination is performed on the scattering body; an illumination unit configured to irradiate an illumination area on a surface of the light scattering body, with the partially coherent light emitted from the light source unit; a detection unit configured to detect, in a detection area including the illumination area, a signal of scattered and returned light from the light scattering body; and an interference component extracting unit configured to extract an interference component by excluding a noninterference component from the signal of the scattered and returned light detected by the detection unit.

In some embodiments, a processing apparatus includes: a light source unit configured to emit partially coherent light having a coherence length that is equal to or more than inverse of a scattering coefficient of a light scattering body and shorter than half of inverse of a reduced scattering coefficient of the light scattering body, the coherence length being a predefined coherence length for a scattering body of the same kind as the light scattering body, the predefined coherence length being defined to generate an interference component within an area showing an intensity of 10% of a maximum intensity of scattered and returned light from a center point of a focused illumination area on the scattering body, among an intensity distribution of internally scattered and returned light that is formed on a surface of the scattering body when focused illumination is performed on the scattering body; an illumination unit configured to irradiate an illumination area on a surface of the light scattering body, with the partially coherent light emitted from the light source unit; a detection unit configured to detect, in a detection area including the illumination area, a signal of scattered and returned light from the light scattering body; and an interference component extracting unit configured to extract an interference component by excluding a noninterference component from the signal of the scattered and returned light detected by the detection unit.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 12 is a schematic diagram illustrating an example in which an interference component signal is acquired by a calculation process;

FIG. 16 is a schematic diagram illustrating image processing of acquiring an interference component signal in the first embodiment;

FIG. 18 is a diagram illustrating the configuration of a principal part of a signal processing apparatus including the light source unit illustrated in FIG. 1;

FIG. 57 is a diagram illustrating a configuration when the first embodiment is applied to a microscope system.

DETAILED DESCRIPTION

Reference will be made below to exemplary embodiments of a processing apparatus for detecting an interference component (speckle) in combination with a medical endoscope system, with reference to the drawings. The present invention is not limited to the embodiments. The same reference signs are used to designate the same elements throughout the drawings. The drawings are schematic drawings, and the relationship between the thickness and the width in each member and the ratio of each member are different from the actual relationship and ratio. Further, the dimension and the ratio may partially differ also between the drawings.

First Embodiment

Figure 1:
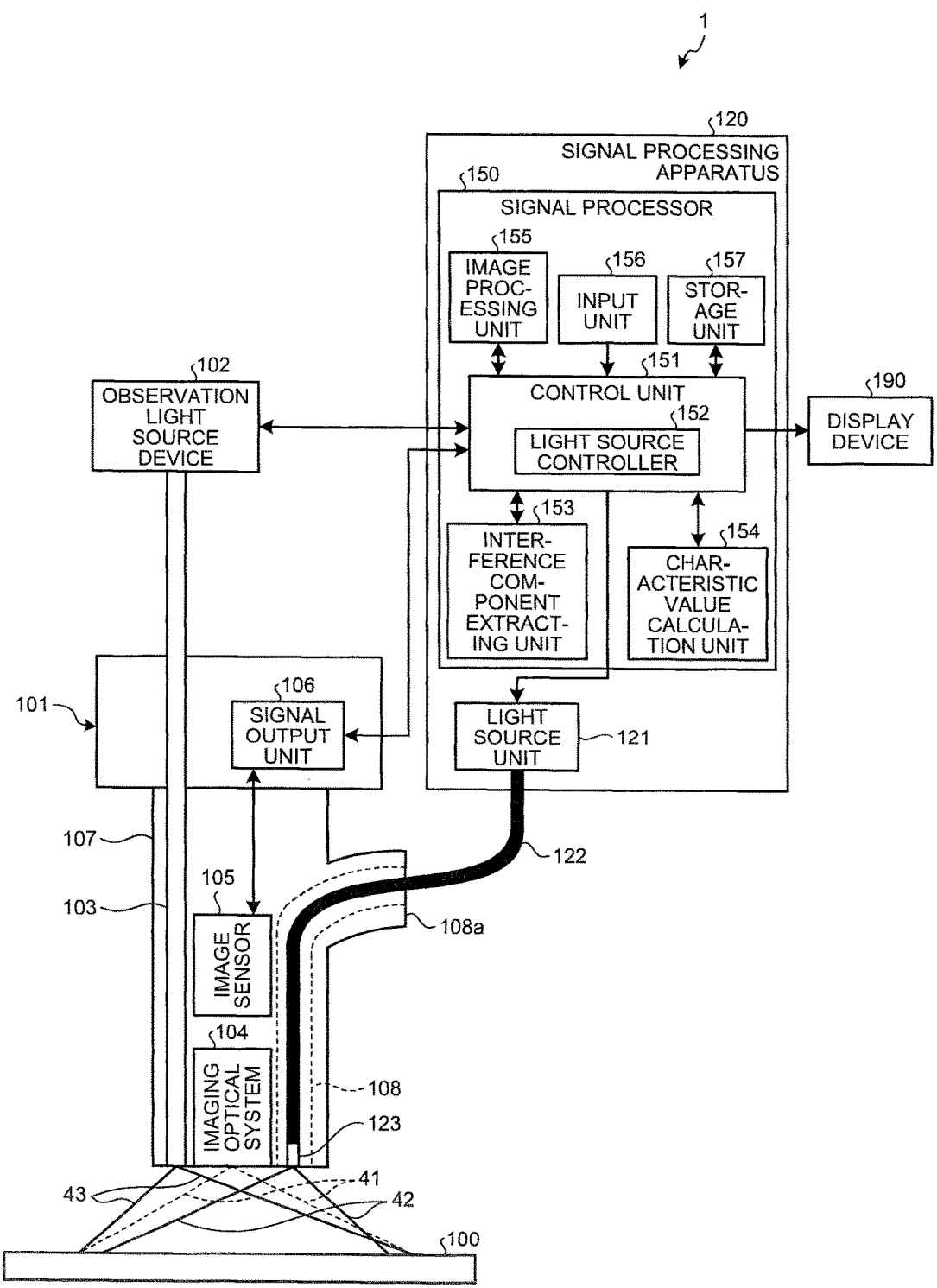
FIG. 1 is a diagram illustrating a schematic configuration of an endoscope system according to a first embodiment of the present invention.

FIG. 1 is a diagram illustrating a schematic configuration of an endoscope system according to a first embodiment of the present invention. As illustrated in FIG. 1, an endoscope system 1 according to the first embodiment is provided with an endoscope apparatus 101 which is introduced into a subject and captures an image of a body tissue 100 inside the subject to generate an image signal of the body tissue 100, an observation light source device 102 which includes a light source such as a white LED and supplies observation light for observing the inside of the subject to the endoscope apparatus 101, a signal processing apparatus 120 (processing apparatus) which emits partially coherent light for acquiring an interference component and processes an image signal of the body tissue 100 during irradiation of the observation light and an image signal of the body tissue 100 during irradiation of the partially coherent light, and a display device 190 which includes, for example, a liquid crystal display or an organic EL display and displays and outputs various pieces of information including image signals processed by the signal processing apparatus 120.

The endoscope apparatus 101 is provided with an observation light guide unit 103, an imaging optical system 104, an image sensor 105 (detection unit), and a signal output unit 106.

The observation light guide unit 103 includes an illumination fiber (light guide cable) and guides observation light supplied from the observation light source device 102 to the distal end of the endoscope apparatus 101.

The imaging optical system 104 includes one or more lenses and forms a subject image on an imaging surface of the image sensor 105 (described below).

The image sensor 105 is provided with a light receiving unit (not illustrated) which includes a plurality of pixels which receives light from the body tissue 100 as a subject and photoelectrically converts the received light to generate an image signal, the pixels being arranged in matrix, a readout unit (not illustrated) which reads an image signal (electric signal) generated by the pixels, and an AFE unit (not illustrated) which performs, for example, noise elimination and A/D conversion on an image signal (analog) read from the image sensor 105. The image sensor 105 is a CCD sensor or a CMOS sensor. An image signal of the surface of the body tissue 100 which is captured by the image sensor 105 when observation light is emitted from the observation light source device 102 is processed as a normal observation image in the signal processing apparatus 120 (described below), and displayed and output from the display device 190. When partially coherent light is emitted from a light source unit 121 (described below), the image sensor 105 functions as a detection unit which detects, in a detection area 41, the intensity of scattered and returned light having been scattered and returned from the body tissue 100, and an image signal of the surface of the body tissue 100 captured in this case is subjected to an interference component extraction process in the signal processing apparatus 120 (described below). In detecting scattered and returned light generated by partially coherent light from the light source unit 121, observation light from the observation light source device 102 is desirably turned off. However, when observation light remaining on does not exceed a detection intensity range of the image sensor 105, scattered light generated by the observation light is also subtracted and eliminated as a noninterference component (described below). Note that the observation light source device is described as a preferred configuration for presenting dynamic information of a body tissue surface layer which is a main object for the present invention in practice more intelligibly than normal observation, and is thus not necessarily required in view of configuration when specialized in dynamic information observation of a body tissue surface layer.

The signal output unit 106 controls the operation of the image sensor 105 in accordance with a control signal received from the signal processing apparatus 120 and outputs an image signal (digital) read from the image sensor 105 to the signal processing apparatus 120.

A casing 107 of the endoscope apparatus 101 is provided with an opening 108a which communicates with a treatment tool channel 108. The distal end of a light guide unit 122 of the signal processing apparatus 120 (described below) is inserted through the opening 108a and reaches an opening on the distal end of the endoscope apparatus 101 through the treatment tool channel 108 formed inside thereof.

The signal processing apparatus 120 functions as a control apparatus which performs predetermined image processing on an image signal captured by the image sensor 105 and controls each unit of the endoscope system 1. Further, the signal processing apparatus 120 also functions as a processing apparatus for irradiating the body tissue 100 as a light scattering body with light satisfying a predetermined condition and extracting an interference component from the intensity of scattered and returned light having been scattered and returned from the body tissue 100 on the basis of an image signal output from the signal output unit 106. The signal processing apparatus 120 is provided with the light source unit 121, the light guide unit 122, an illumination optical system 123 (illumination unit), and a signal processor 150.

The light source unit 121 emits partially coherent light and weak coherent light having a coherence length that is smaller than a coherence length in the partially coherent light. The light source unit 121 emits partially coherent light having a coherence length that is equal to or more than the inverse of a scattering coefficient of the body tissue 100 and shorter than half the inverse of a reduced scattering coefficient of the body tissue 100. The light source unit 121 emits partially coherent light having a predefined coherence length for a scattering body of the same kind as the body tissue 100 to generate an interference component within an area corresponding to an intensity of 10% of the maximum intensity of scattered and returned light from the center point of a focused illumination area in an internally scattered and returned light distribution which is formed on the surface of the scattering body when focused illumination is performed on the scattering body. Here, the scattering body of the same kind means that optical characteristics (light scattering characteristic, light absorption characteristic) thereof with respect to the partially coherent light are substantially equal to the optical characteristics of the body tissue 100. The light source unit 121 emits the partially coherent light and weak coherent light having a coherence length smaller than the coherence length in the partially coherent light. A center wavelength of the partially coherent light and a center wavelength of the weak coherent light are within a visible region or a near infrared region. Scattered and returned light corresponding to the partially coherent light includes a noninterference component together with an interference component. Returned light corresponding to the weak coherent light has a small interference component ratio, and substantially corresponds to a noninterference component depending on setting of the coherence length.

The light guide unit 122 includes an optical fiber and guides light emitted by the light source unit 121. The light guide unit 122 is configured to be inserted through the opening 108a until the distal end of the light guide unit 122 reaches the opening on the distal end of the endoscope apparatus 101 through the treatment tool channel 108 inside the endoscope apparatus 101, and thus, the light guide unit 122 is fixed to the endoscope apparatus 101. The light guide unit 122 includes an optical system which uses one or more optical members such as lenses, and/or one single mode optical fiber or multimode optical fiber or a bundle of single mode optical fibers or multimode optical fibers.

The illumination optical system 123 includes one or more lenses and applies partially coherent light emitted from the light source unit 121 to a predetermined illumination area 42 on the surface of the body tissue 100. The illumination area 42 is set so as to be included in the detection area 41 which is detected by the image sensor 105. Further, an observation area 43 corresponding to observation light from the observation light source device 102 is set within a range which includes the illumination area 42 and the detection area 41.

The signal processor 150 is provided with a control unit 151, an interference component extracting unit 153, a characteristic value calculation unit 154, an image processing unit 155, an input unit 156, and a storage unit 157.

The control unit 151 includes a CPU and controls a processing operation of each unit of the signal processing apparatus 120. The control unit 151 is connected to the endoscope apparatus 101, the observation light source device 102, and the display device 190 through respective cables and also controls a processing operation of each of the connected apparatuses. The control unit 151 is provided with a light source controller 152 which controls a light emission process of the light source unit 121. The light source controller 152 causes the light source unit 121 to emit partially coherent light and weak coherent light at different points in time.

The interference component extracting unit 153 processes an image signal of the surface of the body tissue 100 which is captured by the image sensor 105 when partially coherent light is emitted from the light source unit 121 and eliminates a noninterference component from the intensity of scattered and returned light to extract an interference component. The interference component extracting unit 153 acquires, as an interference component image signal, a subtraction image signal which is obtained by calculating the difference in corresponding parts between an image signal which is captured by the image sensor 105 at an emission timing of partially coherent light by the light source unit 121 and an image signal which is captured by the image sensor 105 at an emission timing of weak coherent light by the light source unit 121.

The characteristic value calculation unit 154 performs a plurality of calculation processes on the basis of an interference component extracted by the interference component extracting unit 153 to calculate characteristic values relating to the properties of the body tissue 100. For example, the characteristic value calculation unit 154 calculates, as the characteristic values, values representing mechanical characteristics such as blood flow in a capillary vessel, the Brownian motion based on the density of a cell, a ciliary motion (ciliary frequency) on the surface of the tunica mucosa bronchiorum, elasticity, viscoelasticity, and hardness.

The image processing unit 155 processes an image signal of the surface of the body tissue 100 which is captured by the image sensor 105 when observation light is emitted from the observation light source device 102 to generate an image signal for normal observation. The image processing unit 155 performs image processing at least including optical black subtraction, white balance (WB) adjustment, image signal synchronization, color matrix calculation, gamma correction, color reproduction, and edge enhancement on an image signal. The image processing unit 155 converts the processed image signal into a display image signal and outputs the display image signal to the display device 190 through the control unit 151.

Accordingly, one in-vivo image is displayed on the display device 190.

The input unit 156 is implemented using an operation device such as a push-type switch, a mouse, a keyboard, or a touch panel and receives input of various pieces of instruction information of the endoscope system 1. Specifically, the input unit 156 receives input of various pieces of instruction information such as subject information, identification information of the endoscope apparatus 101, and test contents.

The storage unit 157 is implemented using a volatile memory or a nonvolatile memory. The storage unit 157 records various programs for operating the signal processing apparatus 120, and various data items and various parameters which are used in interference component extraction processing and image signal processing of normal observation. The storage unit 157 temporarily stores information during processing by the signal processing apparatus 120.

Figure 2:
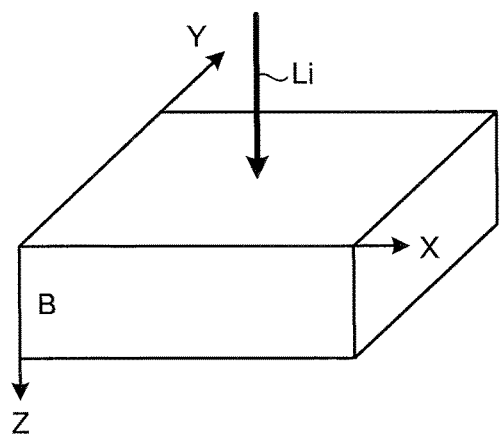
FIG. 2 is a schematic diagram illustrating a scattering body such as body tissues being irradiated with light.
Figure 3:
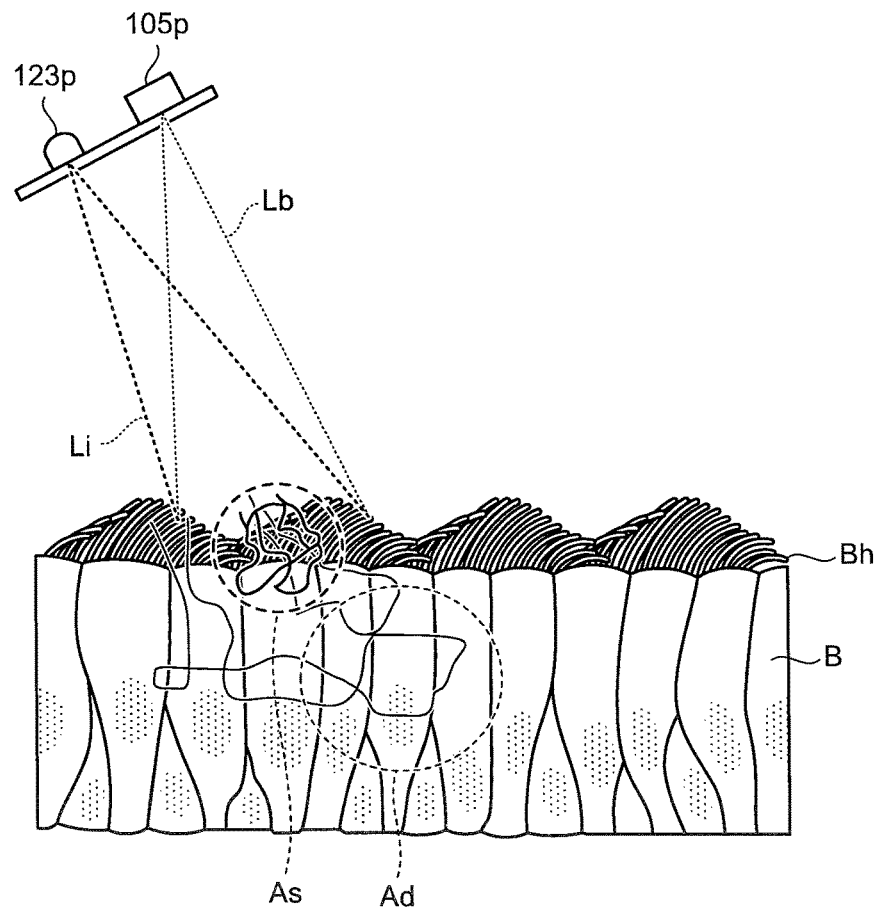
FIG. 3 is a diagram schematically illustrating scattering from the scattering body.
Figure 4:
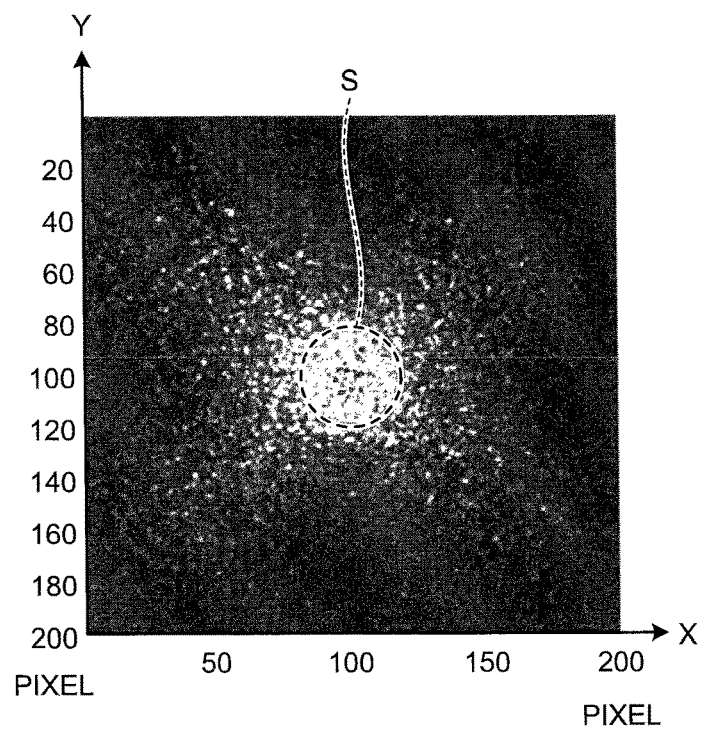
FIG. 4 is an image of the surface of the scattering body which is captured by an image sensor when light is emitted under a conventional condition.

Next, partially coherent light and weak coherent light which are emitted by the light source unit 121 will be described. FIG. 2 is a schematic diagram illustrating a scattering body such as a body tissue being irradiated with light. FIG. 3 is a diagram schematically illustrating a state of light scattering in a scattering body B. FIG. 4 is an image of the surface of the scattering body which is captured by an image sensor 105$p$ when light is emitted under a conventional coherent condition and illustrates an intensity distribution of scattered and returned light Lb (refer to FIG. 3) from the scattering body. FIG. 2 illustrates a case in which partially coherent light Li is emitted by focused illumination from the upper side of the scattering body B in order to acquire scattered and returned light from the scattering body B. In FIG. 2, suppose that the surface of the scattering body B is a plane, any direction in a plane direction is defined as an X direction, a direction perpendicular to the X direction is defined as an Y direction, and a depth direction of the scattering body B is defined as a Z direction. The horizontal axis of FIG. 4 represents the number of pixels in the horizontal direction (X direction) and the vertical axis thereof represents the number of pixels in the vertical direction (Y direction).

Conventionally, a coherence length of the coherent light Li which is applied to the scattering body B from a light source through an illumination optical system 123$p$ is set to be equal to or longer than an optical path length where the light is scattered inside the scattering body B and again returned to the surface. When the movement of a surface layer (an area As of FIG. 3) of the scattering body B is detected under this condition, intensity fluctuations of an interference component based on light scattered from a deep tissue (an area Ad of FIG. 3) of the scattering body B disadvantageously become a disturbance (noise). When viewed in the depth direction (Z direction) of the scattering body B, scattered light that has reached the deep part of the scattering body B affects an interference component on the surface of the scattering body B. Also when viewed in the plane direction (XY direction) of the scattering body B, as illustrated in FIG. 4, interference occurs also in a peripheral direction of the image largely beyond an illumination area S of the partially coherent light on the center of the image. As a result, it is not possible to accurately detect intensity fluctuations of an interference component of scattered and returned light varied by the movement of a cilium Bh or blood on the surface layer of the scattering body B.

Figure 5:
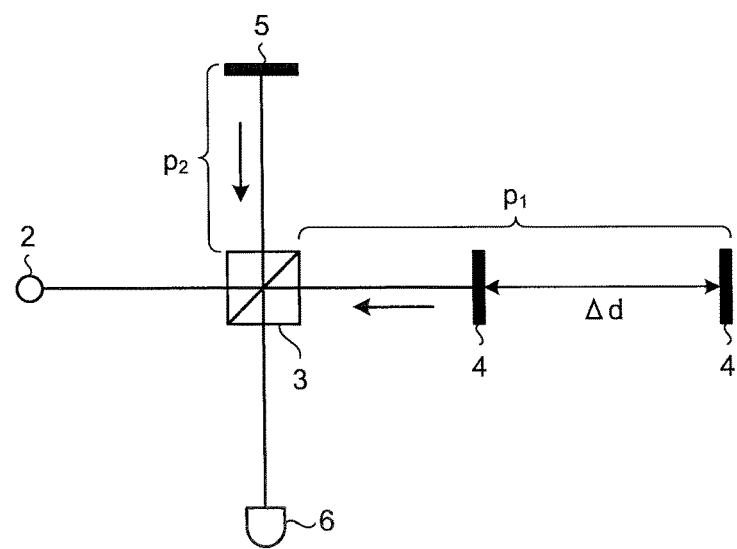
FIG. 5 is a schematic diagram illustrating a Michelson interferometer.

FIG. 5 is a schematic diagram illustrating a Michelson interferometer. As illustrated in FIG. 5, the Michelson interferometer includes a light source 2, a beam splitter 3, a mirror 4, a reference mirror arm 5, and a photo detector 6. The mirror 4 is movable on the same straight line, and a distance $p_1$ from the beam splitter 3 is variable by a distance $\Delta d$ to the outer side from a distance equal to a distance $p_2$ between the reference mirror arm 5 and the beam splitter 3. That is, the distance $\Delta d$ represents the difference in optical path length between two optical paths of the mirror 4 and the reference mirror arm 5.

Figure 6:
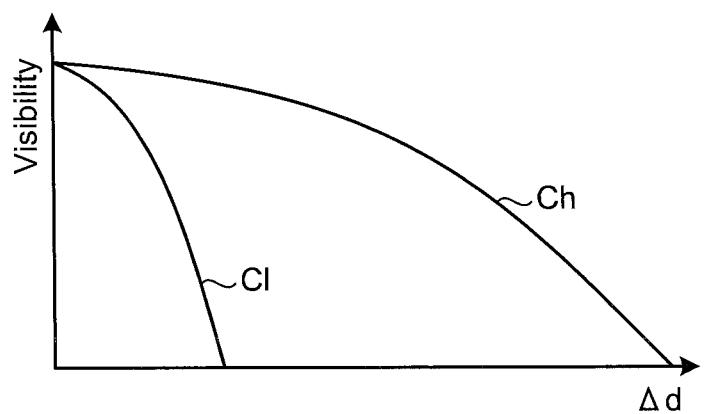
FIG. 6 is a diagram illustrating distance dependence of the visibility of light detected by a photo detector illustrated in FIG. 5.
Figure 7:
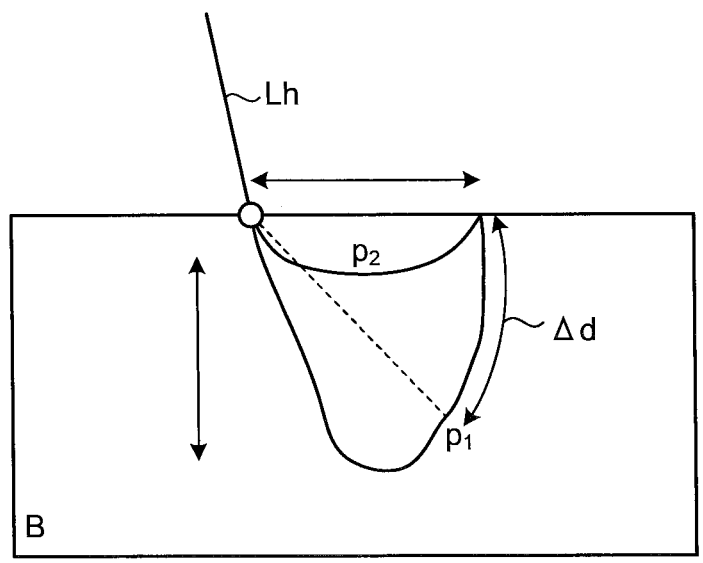
FIG. 7 is a schematic diagram illustrating an optical path inside the scattering body when the scattering body is irradiated with light having a long coherence length.
Figure 8:
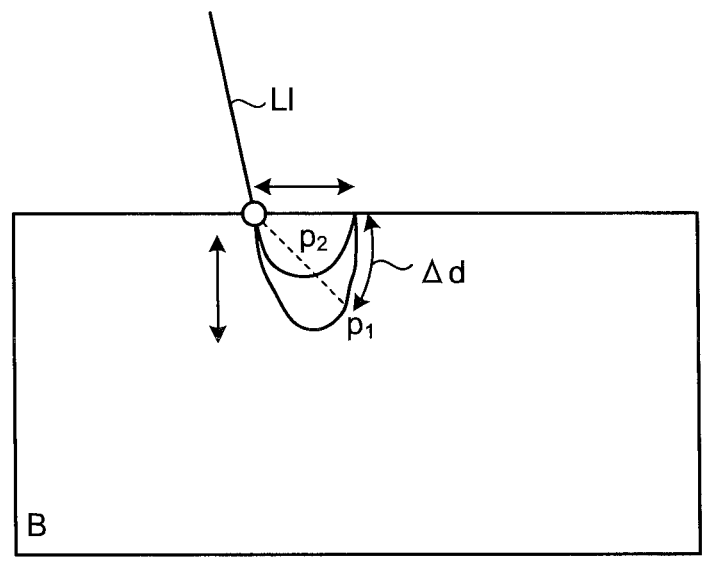
FIG. 8 is a schematic diagram illustrating an optical path inside the scattering body when the scattering body is irradiated with light having a short coherence length.

FIG. 6 is a diagram illustrating dependence of visibility of interference light detected by the photo detector 6 on the optical path length difference $\Delta d$. The visibility is defined by formula (1). When the visibility has a smallest value, interference fringes of the reference mirror arm 5 disappear. A curve Ch of FIG. 6 corresponds to a case in which light Lh having a long coherence length is emitted from the light source 2 and a curve Cl of FIG. 6 corresponds to a case in which a light L1 having a short coherence length is emitted from the light source 2. FIG. 7 is a schematic diagram illustrating an optical path inside the scattering body B when the scattering body B is irradiated with the light Lh having a long coherence length from the light source 2. FIG. 8 is a schematic diagram illustrating an optical path inside the scattering body B when the scattering body B is irradiated with the light L1 having a short coherence length from the light source 2.

$$\text{Visibility} = \frac{I_{max} - I_{min}}{I_{max} + I_{min}} \quad (1)$$

In the case of the emission of the light Lh having a long coherence length to the scattering body B as illustrated in FIG. 7, similarly to the case in which a high visibility is maintained even when the optical path length difference $\Delta d$ between the mirror 4 and the reference mirror arm 5 becomes large in the Michelson interferometer of FIG. 5, even when the optical path length difference $\Delta d$ between the two optical paths $p_1$ and $p_2$ where the light is scattered inside the scattering body B and returned to the surface becomes large, light transmitted through the optical path $p_1$ and light transmitted through the optical path $p_2$ interfere with each other on the surface of the scattering body B and form an interference pattern (speckle). On the other hand, in the case of the emission of the light L1 having a short coherence length to the scattering body B as illustrated in FIG. 8, similarly to the case in which the visibility is reduced also when the optical path length difference $\Delta d$ between the mirror 4 and the reference mirror arm 5 in the Michelson interferometer of FIG. 5 is smaller than that in the case of FIG. 7, interference occurs on the surface of the scattering body B only when the optical path length difference $\Delta d$ between the two optical paths $p_1$ and $p_2$ where the light is scattered inside the scattering body B and returned to the surface is small. When the light Lh is emitted as illustrated in FIG. 7, the coherence length is long. Thus, scattered light beams that have reached various depths including a deep part of the scattering body B interfere with each other, which contributes to the formation of an interference component pattern on the surface of the scattering body B. In other words, also on the surface of the scattering body B, an interference component pattern by multiple scattering is formed up to a range away from an illumination point on the surface of the scattering body B. On the other hand, when the light L1 is emitted as illustrated in FIG. 8, since the coherence length is short, only a pair of scattered light beams having a small optical path length difference $\Delta d$ interfere with each other. As a result, light beams that are scattered from the surface layer part largely contribute to the formation of an interference pattern on the surface of the scattering body B. Thus, when the light L1 having a short coherence length is emitted, an interference component pattern is formed only immediately near the illumination point on the surface of the scattering body B. This means that, in order to reduce the influence of scattered light that has reached the deep part of the body tissue and becomes noise to acquire an interference component which is based only on scattered and returned light having been scattered and returned from the surface layer of the body tissue, it is necessary to adjust a coherence length of low coherent light to be applied.

Figure 9:
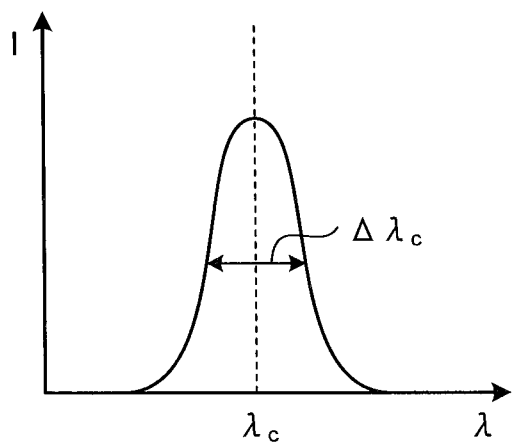
FIG. 9 is a schematic diagram illustrating the relationship between the coherence length and a light source wavelength width.

Thus, in the first embodiment, the coherence length of low coherent light applied to the body tissue 100 is set such that an interference component based on scattered and returned light having been scattered and returned from the surface layer of the body tissue can be acquired in both the depth direction of the body tissue and the surface direction of the body tissue. First, the coherence length will be described. The coherence length is an index indicating the coherence of a light source. Here, the coherence length is defined by the optical path length difference Δd with which the interference light visibility observed using the Michelson interferometer of FIG. 5 becomes $\sqrt{(1/2)}$. Further, FIG. 9 is a schematic diagram illustrating the coherence length using the wavelength width of the light source and illustrates an example of a wavelength distribution (power spectrum) of the intensity (I) of partially coherent light which is applied to the body tissue 100. In the partially coherent light illustrated in FIG. 9, a coherence length $L_c$ is defined by formula (2) using a center wavelength $\lambda_c$ of light emitted by the light source and a wavelength width $\Delta\lambda_c$ which is a full width at half maximum (FWHM).

$$L_c = \frac{2\ln 2 \lambda_c^2}{\pi \Delta \lambda_c} \qquad (2)$$

Figure 10A:
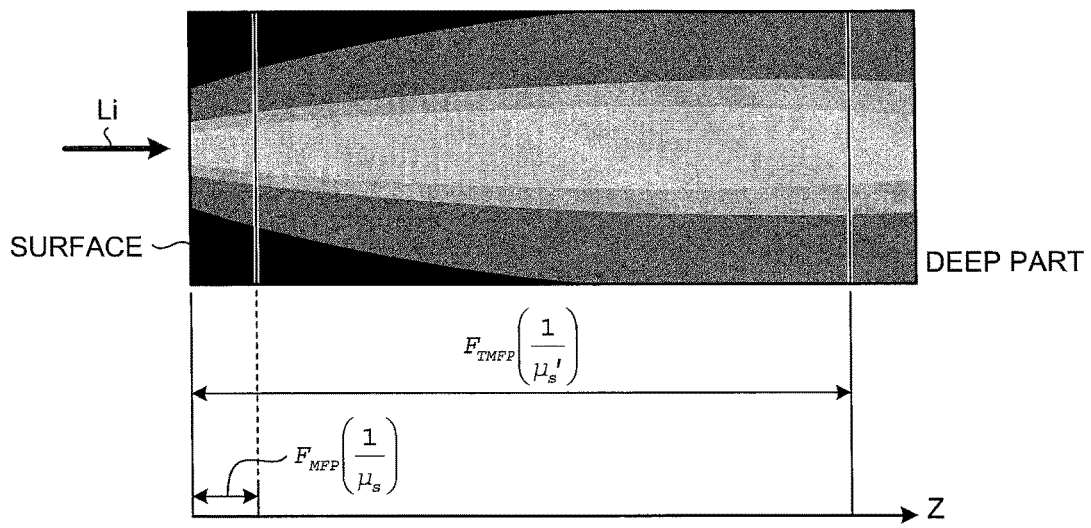
FIG. 10A is a schematic diagram illustrating light propagation (light scattering) inside the scattering body.
Figure 10B:
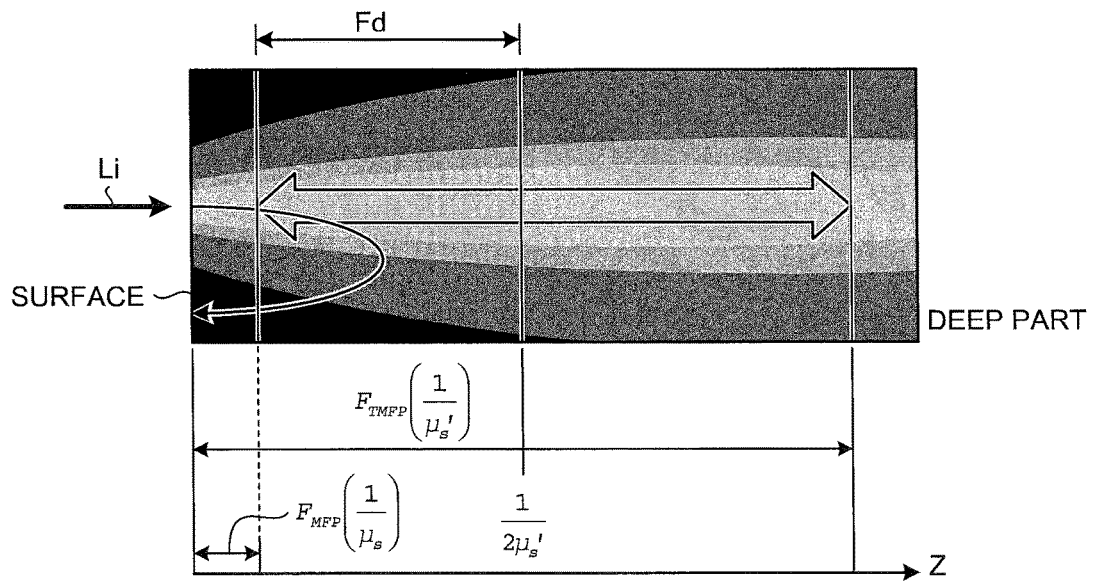
FIG. 10B is a schematic diagram illustrating the relationship between the light propagation (light scattering) inside the scattering body and the coherence length.

In the first embodiment, in order to detect an interference component, the light source unit 121 emits partially coherent light having a coherence length $L_c$ that is equal to or more than the inverse of the scattering coefficient of the body tissue 100 which is a light scattering body and shorter than half the inverse of the reduced scattering coefficient of the body tissue 100 to the scattering body B such as a body tissue. FIGS. 10A and 10B are diagrams for describing the coherence length $L_c$ of the partially coherent light emitted from the light source unit 121. The horizontal axis of FIGS. 10A and 10B represents the depth direction (Z direction) of the scattering body B. FIGS. 10A and 10B are diagrams schematically illustrating a state in which the surface of the scattering body B is irradiated with beam light as illumination light Li and the light is scattered inside the scattering body B.

The scattering coefficient is an amount representing how many times scattering occurs inside the scattering body per unit thickness and denoted by $\mu_s$ [mm$^{-1}$] in the first embodiment. The inverse of the scattering coefficient $\mu_s$ (mean free path (MFP)) represents the distance that a photon travels inside the scattering body while scattering occurs once and corresponds to a depth $F_{MFP}$ from the surface in FIGS. 10A and 10B. The reduced scattering coefficient is an amount representing how many times scattering of a photon occurs until light is scattered inside the scattering body so as to lose the directivity and denoted by $\mu_s'$ [mm] in the first embodiment. The inverse of the reduced scattering coefficient $\mu_s'$ (transport mean free path (TMFP)) represents the distance until light is sufficiently scattered inside the scattering body so as to lose the directivity and corresponds to a depth $F_{TMFP}$ from the surface in FIGS. 10A and 10B. The reduced scattering coefficient $\mu_s'$ is defined by formula (3) using a parameter g which represents a traveling direction of light, that is, the parameter g which represents an anisotropy factor of light and the scattering coefficient $\mu_s$.

$$\mu_s' = (1-g)\mu_s \qquad (3)$$

In order for incident light to return to the incident direction, it is required that the light scatter at least once. In this case, when the coherence length $L_c$ is smaller than the MFP, formation of an interference component on the surface is not performed by scattered and returned light. Thus, it is required that the coherence length $L_c$ of partially coherent light emitted from the light source unit 121 be equal to or more than the MFP. Further, light that has returned from a part deeper than the TMFP is an excessive multiple scattering component. The multiple scattering component forms no interference component and becomes noninterference background by making the coherence length smaller than the TMFP, and only information at a depth within the TMFP can be extracted as an interference component. Thus, the coherence length $L_c$ of partially coherent light emitted from the light source unit 121 is required to be equal to or more than the inverse of the scattering coefficient $\mu_s$ of the body tissue 100 which is a light scattering body and shorter than the inverse of the reduced scattering coefficient $\mu_s'$ of the body tissue 100. Further, since the parameter g which represents the anisotropy factor of light satisfies 0<g<1 in the body tissue 100 to be examined, the inverse of the reduced scattering coefficient $\mu_s'$ never becomes larger than the inverse of the scattering coefficient $\mu_s$.

Figure 11A:
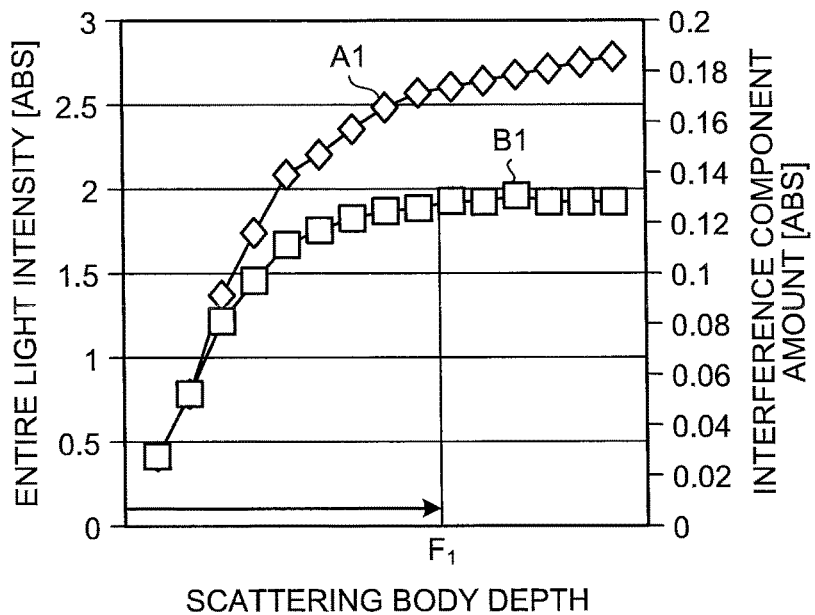
FIG. 11A is a diagram illustrating scattering body depth dependence of the entire light intensity and the interference component amount when partially coherent light having a predetermined coherence length is emitted.
Figure 11B:
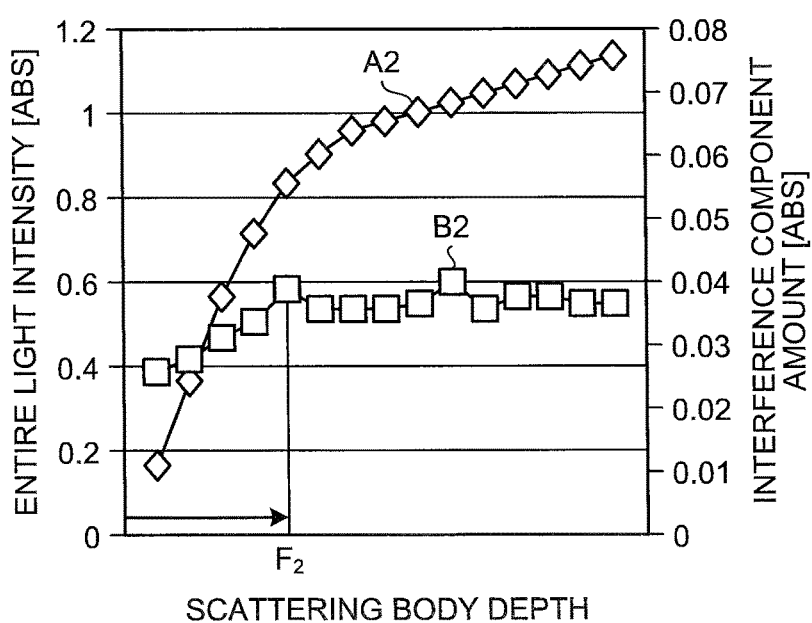
FIG. 11B is a diagram illustrating scattering body depth dependence of the entire light intensity and the interference component amount when partially coherent light having a predetermined coherence length is emitted.
Figure 11C:
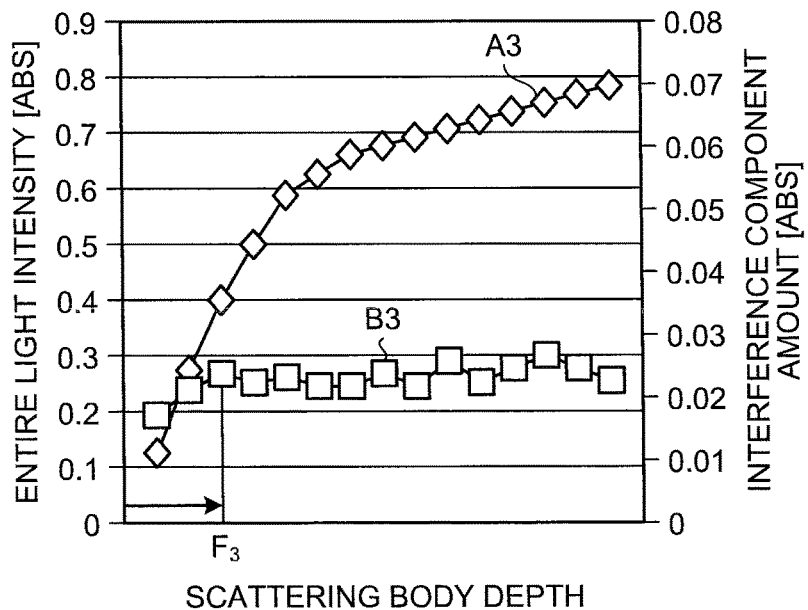
FIG. 11C is a diagram illustrating scattering body depth dependence of the entire light intensity and the interference component amount when partially coherent light having a predetermined coherence length is emitted.
Figure 11D:
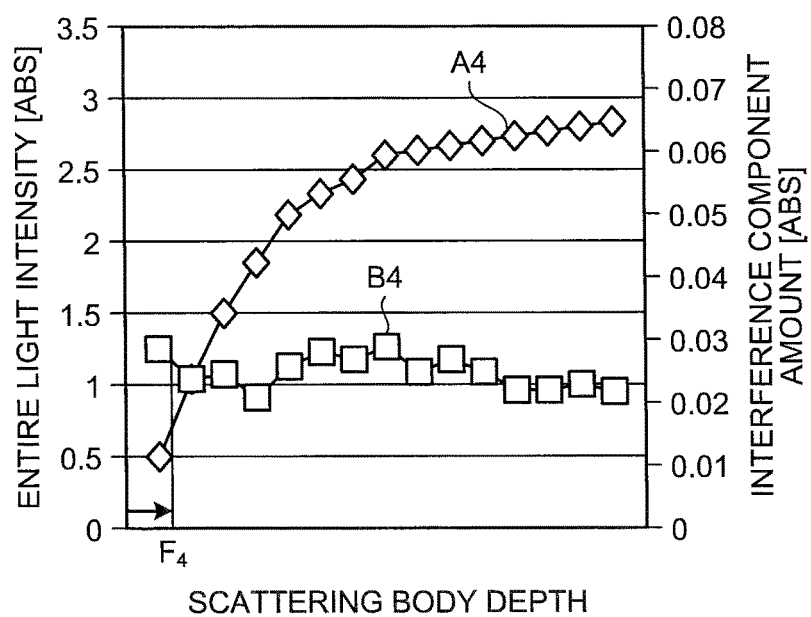
FIG. 11D is a diagram illustrating scattering body depth dependence of the entire light intensity and the interference component amount when partially coherent light having a predetermined coherence length is emitted.

A result of a generation state of an interference component which is actually obtained by changing the coherence length $L_c$ of partially coherent light emitted from the light source unit 121 will be described. First, a generation state of an interference component in the depth direction of the body tissue will be described with reference to FIGS. 11A to 11D. FIGS. 11A to 11D are diagrams illustrating changes in the entire light intensity and the interference component amount (the difference between the maximum intensity and the minimum intensity of interference light) of scattered and returned light which is generated on the surface by changing the thickness (depth) of the scattering body with respect to the condition of each coherence length $L_c$. A curve A1 of FIG. 11A represents the entire light intensity of scattered and returned light (entire light intensity) when partially coherent light having a coherence length $L_{t1}$ is emitted, and a curve B1 represents the interference component amount therein. A curve A2 of FIG. 11B represents the entire light intensity when partially coherent light having a coherence length $L_{t2}$ is emitted, and a curve B2 represents the interference component amount therein. A curve A3 of FIG. 11C represents the entire light intensity when partially coherent light having a coherence length $L_{t3}$ is emitted, and a curve B3 represents the interference component amount therein. A curve A4 of FIG. 11D represents the entire light intensity when partially coherent light having a coherence length $L_{t4}$ is emitted, and a curve B4 represents the interference component amount therein. The coherence lengths $L_{t1}$ to $L_{t4}$ have a relationship of $L_{t1} > L_{t2} > L_{t3} > L_{t4}$.

When the scattering body thickness is gradually increased, the interference component amount on the surface increases while scattered and returned light that has reached the deepest layer contributes to interference on the surface. When the scattering body thickness becomes equal to or more than a certain thickness and contribution of scattered and returned light that has reached a deep part to interference on the surface is stopped, the entire light intensity continuously increases with the increase in the thickness of the scattering body, but, on the other hand, the interference component amount remains unchanged even when the scattering body thickness is increased. A depth where the interference component amount becomes saturated is a depth $F_1$ (refer to FIG. 11A) in the case of the coherence length $L_{t1}$, a depth $F_2$ ($<F_1$) (refer to FIG. 11B) in the case of the coherence length $L_{t2}$, a depth $F_3$ ($<F_2$) (refer to FIG. 11C) in the case of the coherence length $L_{t3}$, and a depth $F_4$ ($<F_3$) (refer to FIG. 11D) in the case of the coherence length $L_{t4}$. Thus, the interference component amount converges at a deeper position as the coherence length is longer and converges at a shallower position as the coherence length is shorter. That is, in the interference component amount, a depth having a sensitivity differs depending on the coherence length. Thus, the coherence length $L_c$ of partially coherent light emitted from the light source unit 121 may be adjusted with respect to the body tissue 100 to be examined according to the depth from the surface where an interference component is desired to be acquired.

Each scattering characteristic value of the body tissue 100 as a parameter represented by formula (3) and formula (4) (described below) can be measured previously with respect to a scattering body of the same kind as the body tissue 100, using a measurement method based on a front scattering intensity and a back scattering intensity using two integrating spheres, a measurement and evaluation method based on the spatial distribution of a back scattering intensity using a single fiber or a fiber array, or a measurement method based on the OCT intensity distribution. The scattering characteristic value of the body tissue 100 varies also depending on the wavelength of illumination light. Thus, it is necessary to determine an illumination light condition (wavelength width) for obtaining the coherence length that satisfies the condition in the first embodiment for each illumination wavelength.

A generation state of an interference component on the surface of the body tissue will be described. FIG. 12 is a schematic diagram illustrating an example in which an interference component signal is acquired by a calculation process. An image signal Gs which is obtained by performing spot lighting on the body tissue surface with partially coherent light and subtracting a signal Gm which is generated by applying median filtering to an image signal Go which is obtained by capturing an image of a certain area including an illumination area S of the partially coherent light illustrated in FIG. 12 from the image signal Go in corresponding parts corresponds to a signal representing an interference component signal. The width in the horizontal direction of the illumination area S is denoted by Sx.

Figure 13A:
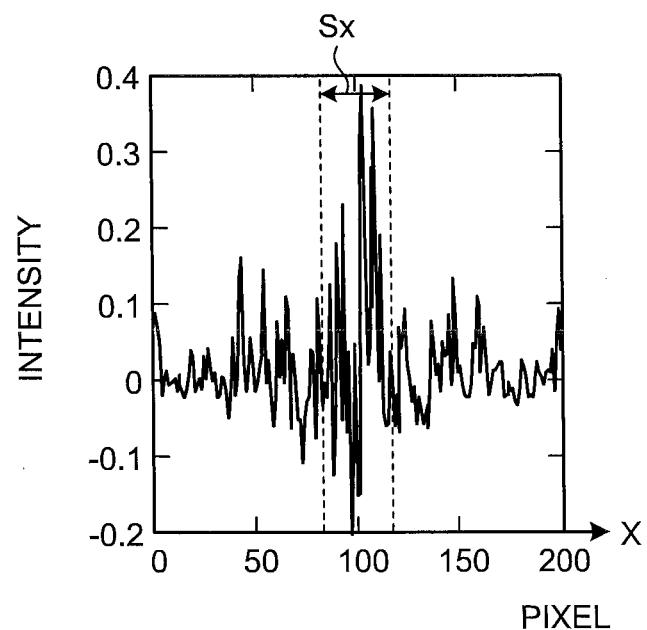
FIG. 13A is a diagram illustrating an example of an intensity distribution in a horizontal line which passes through the center of an illumination area in an image signal illustrated in FIG. 12.
Figure 13B:
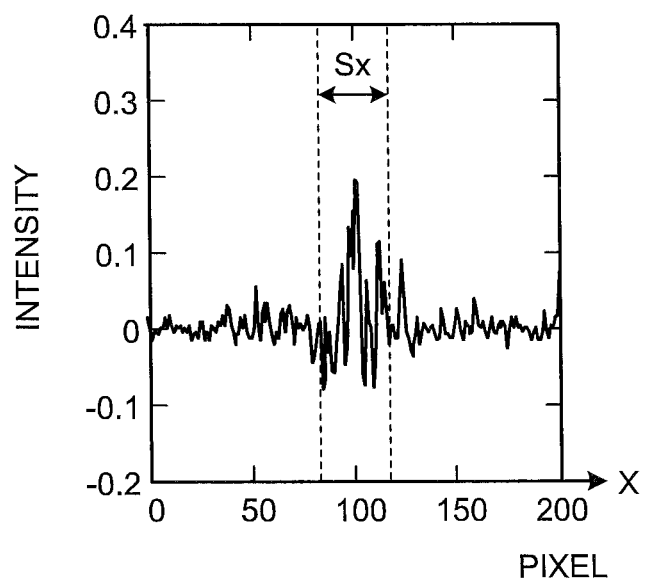
FIG. 13B is a diagram illustrating an example of the intensity distribution in the horizontal line which passes through the center of the illumination area in the image signal illustrated in FIG. 12.
Figure 13C:
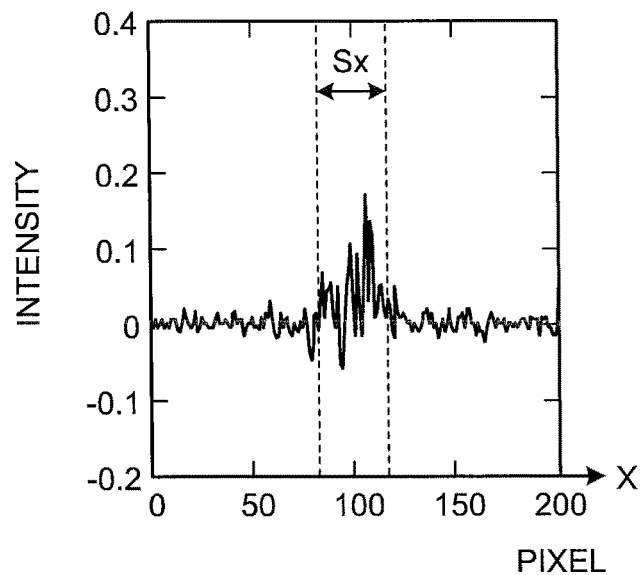
FIG. 13C is a diagram illustrating an example of the intensity distribution in the horizontal line which passes through the center of the illumination area in the image signal illustrated in FIG. 12.
Figure 13D:
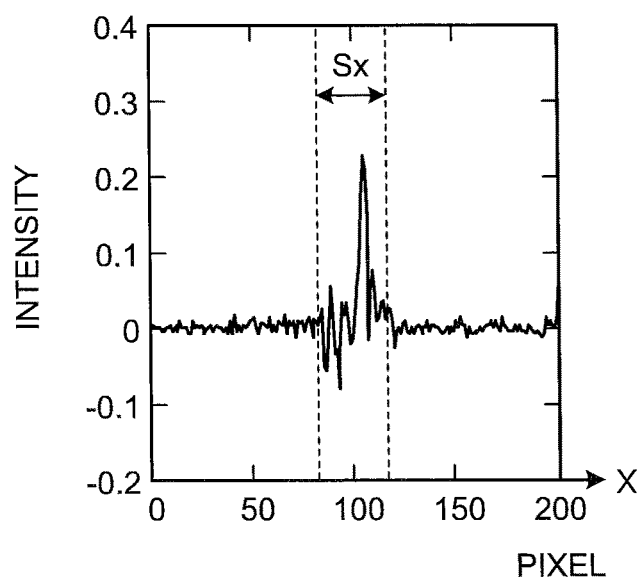
FIG. 13D is a diagram illustrating an example of the intensity distribution in the horizontal line which passes through the center of the illumination area in the image signal illustrated in FIG. 12.

FIGS. 13A to 13D are diagrams illustrating the intensity distribution in a horizontal line in the Y direction which passes through the center of the illumination area S and has a width Ya in the image signal Gs illustrated in FIG. 12. In FIGS. 13A to 13D, the horizontal axis represents the number of pixels in the horizontal direction of the image signal Gs, and the vertical axis represents the intensity of scattered and returned light. FIG. 13A illustrates an intensity distribution in the case where partially coherent light having the coherence length $L_{t1}$ is emitted, FIG. 13B illustrates an intensity distribution in the case where partially coherent light having the coherence length $L_{t2}$ is emitted, FIG. 13C illustrates an intensity distribution in the case where partially coherent light having the coherence length $L_{t3}$ is emitted, and FIG. 13D illustrates an intensity distribution in the case where partially coherent light having the coherence length $L_{t4}$ is emitted.

As illustrated in FIGS. 13A to 13D, the generation of an interference component is limited to the proximity of the width Sx of the illumination area S with a shorter coherence length, and an interference component is generated in a wide range beyond the width Sx of the illumination area S with a longer coherence length. Similarly, also in the body tissue surface, the generation area of an interference component varies depending on the coherence length. In other words, the generation of an interference signal can be controlled within a range immediately near the illumination area S with a shorter coherence length, and the generation of an interference component expands to a range largely beyond the illumination area S with a longer coherence length.

Thus, in the first embodiment, the coherence length $L_c$ of partially coherent light emitted from the light source unit 121 is set so as to stably generate an interference component only in an area near the illumination area of the partially coherent light on the surface layer of the body tissue 100 in both the depth direction of the body tissue 100 and the plane direction of the surface of the body tissue 100. First, in the first embodiment, as a condition corresponding to the depth direction of the body tissue, the upper limit of the coherence length $L_c$ of the partially coherent light emitted from the light source unit 121 is set so as to be further limited to a value that is shorter than half the inverse of the reduced scattering coefficient $\mu_s'$ of the body tissue 100 to be examined (the right end of a depth range Fd of FIG. 10B) so that the interference component amount reliably converges at a shallow position in the body tissue 100. That is, the coherence length $L_c$ of the partially coherent light emitted from the light source unit 121 is defined by the following formula (4).

$$\frac{1}{\mu_s} \le L_c < \frac{1}{2\mu_s'} \qquad (4)$$

Figure 14:
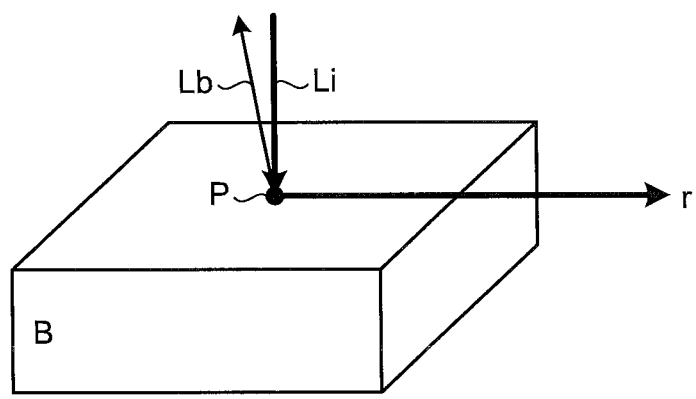
FIG. 14 is a schematic diagram illustrating a method for adjusting the coherence length of partially coherent light emitted from a light source unit illustrated in FIG. 1.

Further, as a condition corresponding to the plane direction of the surface of the body tissue 100, the coherence length $L_c$ of the partially coherent light emitted from the light source unit 121 is set to a predefined coherence length for a scattering body of the same kind as the body tissue 100 to generate an interference component within an area corresponding to an intensity of 10% of the maximum intensity from the center point of the focused illumination area in the intensity distribution of internally scattered and returned light which is formed on the surface of the scattering body when focused illumination is performed on the scattering body. FIG. 14 is a schematic diagram illustrating a method for adjusting the coherence length $L_c$ of the partially coherent light emitted from the light source unit 121. In practice, as illustrated in FIG. 14, previously, a point area P on the surface of the scattering body B of the same kind as the body tissue 100 to be examined is irradiated with beams of partially coherent light Li having different coherence lengths $L_c$, and an intensity distribution of each internally scattered and returned light Lb returned at this time is detected.

Figure 15:
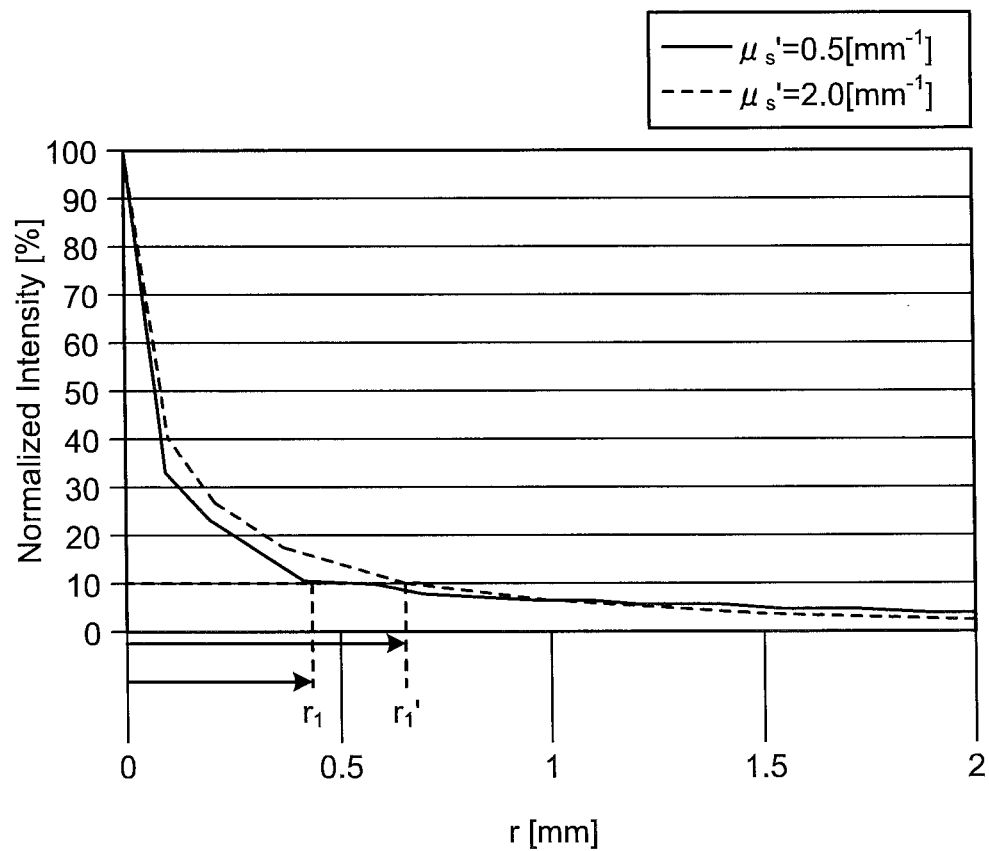
FIG. 15 is a diagram illustrating intensity dependence of internally scattered and returned light in an r direction illustrated in FIG. 14.

FIG. 15 is a diagram illustrating intensity dependence of internally scattered and returned light in an r direction illustrated in FIG. 14. In FIG. 15, zero in the r direction corresponds to the center point of the point area P. As illustrated in FIG. 15, the internally scattered and returned light has an intensity distribution in which the intensity attenuates due to scattering as the distance from the illumination point increases. FIG. 15 illustrates, as an example for reference, a result of the internally scattered and returned light intensity distribution obtained by a Monte Carlo simulation for cases in which the reduced scattering coefficient $\mu_s'$ in the body tissue is 0.5 mm$^{-1}$ (solid line) and 2.0 mm$^{-1}$ (broken line). Further, in FIG. 15, the intensity (I) in the vertical axis does not include the intensity of directly reflected light from the surface of the scattering body B. As illustrated in FIG. 15, a coherence length that generates an interference component within a distance $r_1$ corresponding to an intensity of 10% of the maximum intensity of scattered and returned light from the center point (r=0) of the focused illumination area is obtained, and the obtained coherence length is set as the coherence length $L_c$ of the partially coherent light emitted from the light source unit 121. As illustrated in FIG. 15, in the intensity distribution of scattered and returned light, the intensity suddenly attenuates from the center point (r=0) of the focused illumination area, and scattered light is detected even at a position away from the center point by 1 mm or more. Limiting the generation of an interference component within the distance $r_1$ corresponding to an intensity of 10% of the maximum intensity of scattered and returned light makes it possible to limit spatial expansion in the plane direction which is detected as an interference component to a range smaller than 1 mm. Thus, even when an illumination area pattern is a uniform pattern or a multipoint pattern as described below, it is possible to make a spatial resolution of a signal extracted as an interference component smaller than 1 mm. Although the distance corresponding to the intensity of 10% of the maximum intensity of scattered and returned light varies ($r_1$, $r_1'$ in FIG. 15) to some extent according to the reduced scattering coefficient $\mu_s'$ of the body tissue 100, the present effect can be practically obtained by determining a set value using the scattering body B of the same kind within the range of variations of the body tissue.

In practice, as illustrated in FIG. 16, similarly to the procedure described with reference to FIG. 12, an intensity distribution of scattered and returned light in a horizontal line which passes through the center of a predetermined area Sc and has a width Ya in an image signal Gs is acquired. The image signal Gs is obtained by performing spot lighting on the surface of the scattering body B of the same kind as the body tissue 100 to be examined with partially coherent light and subtracting a signal Gm which is generated by applying median filtering to an image signal Go which is obtained by capturing an image of a certain area including a spot area of the partially coherent light from the image signal Go in corresponding parts. The area Sc in FIG. 16 corresponds to an area corresponding to an intensity of 10% of the maximum intensity of scattered and returned light from the center point of the illumination area S (refer to FIG. 12) as a focused illumination area. The width in the horizontal direction of the area Sc is denoted by Scx.

Figure 17A:
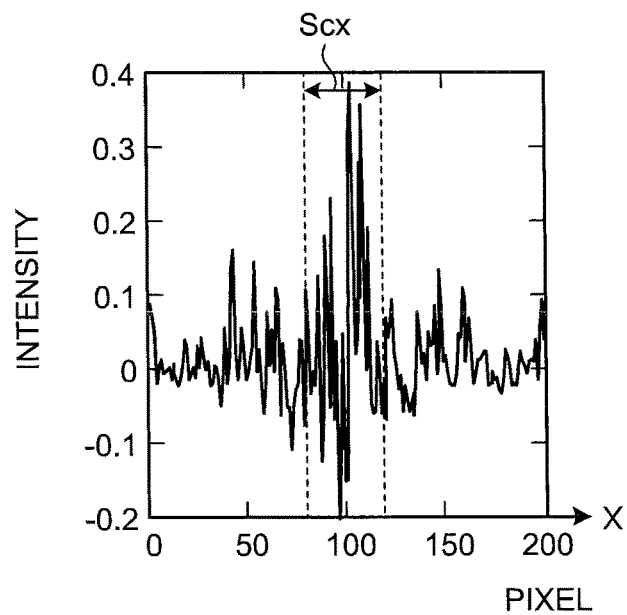
FIG. 17A is a diagram illustrating an intensity distribution in a horizontal line which passes through the center of an illumination area in an image signal illustrated in FIG. 16.
Figure 17B:
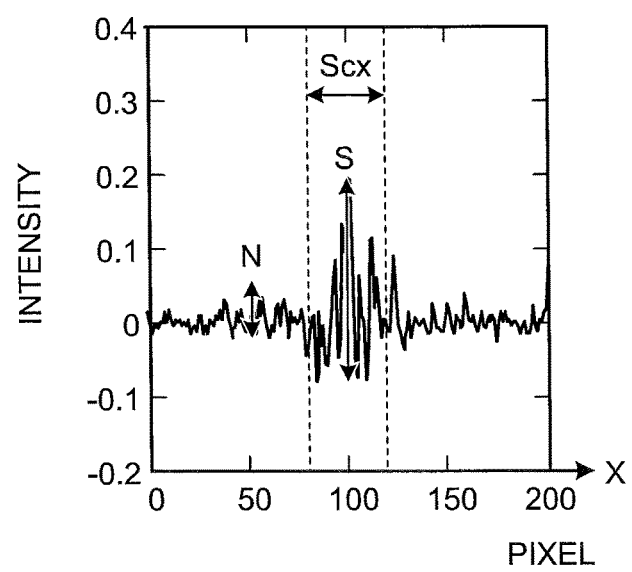
FIG. 17B is a diagram illustrating an intensity distribution in the horizontal line which passes through the center of the illumination area in the image signal illustrated in FIG. 16.
Figure 17C:
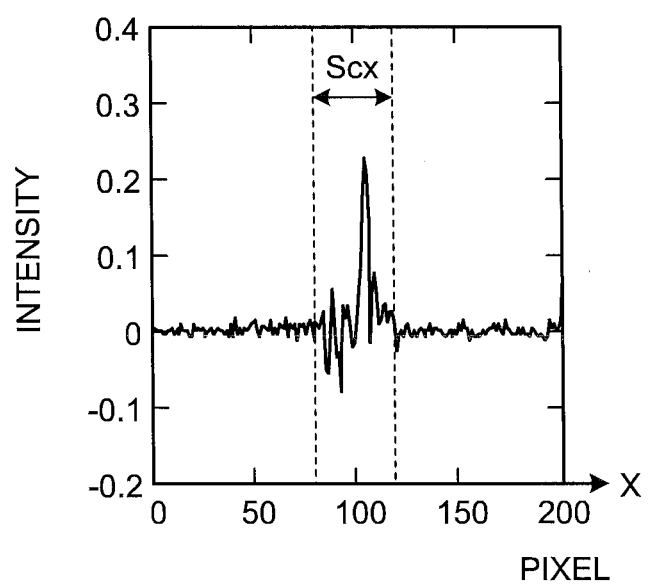
FIG. 17C is a diagram illustrating an intensity distribution in the horizontal line which passes through the center of the illumination area in the image signal illustrated in FIG. 16.

FIGS. 17A to 17C are diagrams illustrating the intensity distribution in the horizontal line in the Y direction which passes through the center of the area Sc and has the width Ya in the image signal Gs illustrated in FIG. 16. Also in FIGS. 17A to 17C, similarly to FIGS. 13A to 13C, the horizontal axis represents the number of pixels in the horizontal direction of the image signal Gs, and the vertical axis represents the intensity of scattered and returned light. FIG. 17A illustrates an intensity distribution in the case where partially coherent light having the coherence length $L_{t1}$ is emitted, FIG. 17B illustrates an intensity distribution in the case where partially coherent light having the coherence length $L_{t2}$ is emitted, and FIG. 17C illustrates an intensity distribution in the case where partially coherent light having the coherence length $L_{t3}$ is emitted. In the first embodiment, an S/N ratio is acquired in each intensity distribution, and a coherence length in which the S/N ratio is equal to or more than 10 or an N value is equal to or less than a detection system noise is selected. In the examples of FIGS. 17A to 17C, the S/N ratio is equal to or more than 10 or the N value is equal to or less than the detection system noise with the coherence length $L_{t3}$. Thus, the coherence length $L_{t3}$ is selected as the coherence length $L_c$ of the partially coherent light applied to the body tissue 100. In practice, with partially coherent light having the coherence length $L_{t3}$ selected in this manner, the generation of an interference component is substantially limited within the width Scx of the area corresponding to the intensity of 10% of the maximum intensity of scattered and returned light from the center point of the focused illumination area in the internally scattered and returned light (refer to FIG. 17C).

The body tissue 100 to be examined is typically a mucosal layer on the surface layer of a luminal organ such as the small intestine, the large intestine, or the bronchial tube, a tissue surface which is an observation object during a surgery, or a tissue surface exposed by an incision, and the range of the reduced scattering coefficient $\mu_s'$ is 0.5 to 2.0 [mm$^{-1}$], and the range of the parameter g is 0.80 to 0.99. When detection is actually performed by applying partially coherent light whose coherence length $L_c$ is set to the range defined by formula (4) to the mucosal layer on the surface layer of an alimentary canal, it is possible to stably detect an interference component that is generated only on the surface layer of the body tissue 100 to be examined. Further, also when detection is performed by irradiating the surface layer of the body tissue 100 with partially coherent light having a coherence length $L_c$ that is predefined for a scattering body of the same kind as the body tissue 100 to be examined and that generates an interference component within the area corresponding to an intensity of 10% of the maximum intensity of scattered and returned light from the center point of the focused illumination area in the internally scattered and returned light distribution which is formed on the surface of the scattering body when focused illumination is performed on the scattering body, it is possible to stably detect an interference component that is generated only on the surface layer of the body tissue 100. The partially coherent light applied to the body tissue 100 may be set so as to satisfy both the condition of setting the coherence length $L_c$ to the range defined by formula (4) and the condition that an interference component is generated within the area corresponding to an intensity of 10% of the maximum intensity of scattered and returned light from the center point of the focused illumination area in the internally scattered and returned light distribution which is formed on the surface of a scattering body of the same kind as the body tissue 100 when focused illumination is performed, or may be set so as to satisfy only one of the conditions.

Next, the configuration of the light source unit 121 will be described. FIG. 18 is a diagram illustrating the configuration of a principal part of the signal processing apparatus 120 including the light source unit 121. As described above, the light source unit 121 emits partially coherent light and weak coherent light which has a coherence length smaller than the coherence length of the partially coherent light in a temporally switching manner.

The light source unit 121 includes a broadband laser (SLD) 124, a filter wheel 125, a collimator lens 126, a focus lens 127, and a controller 129. The proximal end of an optical fiber 128 is disposed on a focal position of the focus lens 127. Light passed through the filter wheel 125, the collimator lens 126, and the focus lens 127 is transmitted by the optical fiber 128 to the illumination optical system 123 on the distal end of the optical fiber 128 and emitted to the outside. One single mode (SM) optical fiber or multimode (MM) optical fiber or a bundle of single mode optical fibers or multimode optical fibers is used as the optical fiber 128.

The SLD 124 emits broadband light of a band including at least a wavelength band of the partially coherent light whose coherence length $L_c$ is defined in the above manner and a wavelength band of the weak coherent light.

The filter wheel 125 (moving unit) includes a band pass filter (BPF, a first filter) for passing light of a wavelength band of the partially coherent light and a neutral density filter (NDF, a second filter) for passing light of a wavelength band of the weak coherent light. The filter wheel 125 is capable of switching a filter to be disposed on an optical path of light emitted by the SLD 124 between the BPF and the NDF. The filter wheel 125 is, for example, a rotary filter having a rotatable plate-like shape and capable of moving the BPF or the NDF onto the optical path of light emitted by the SLD 124 by rotation. The controller 129 controls a filter switching operation of the filter wheel 125 under the control of the light source controller 152.

Figure 19:
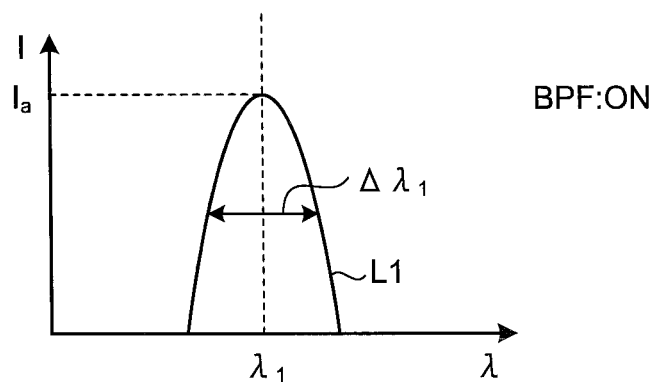
FIG. 19 is a diagram illustrating wavelength dependence of light emitted from a filter wheel illustrated in FIG. 18.
Figure 20:
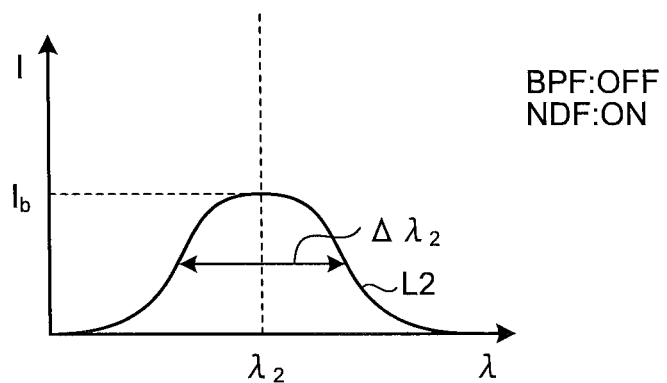
FIG. 20 is a diagram illustrating wavelength dependence of light emitted from the filter wheel illustrated in FIG. 18.

FIGS. 19 and 20 are diagrams illustrating dependence of the intensity (I) of light emitted from the filter wheel 125 on wavelength (λ). As illustrated in FIG. 19, when the BPF is ON, that is, when the BPF is disposed on the optical path of light emitted by the SLD 124, partially coherent light L1 which has a center wavelength $\lambda_1$, a full width at half maximum $\Delta\lambda_1$, and a coherence length $L_c$ defined in the above manner is emitted. Further, as illustrated in FIG. 20, when the BPF is OFF and the NDF is ON, that is, when the NDF is disposed on the optical path of light emitted by the SLD 124, weak coherent light L2 which has a center wavelength $\lambda_2$ and a full width at half maximum $\Delta\lambda_2$ is emitted. In the light source unit 121, for simplifying a calculation process in the interference component extracting unit 153, the total amount of the partially coherent light L1 and the total amount of the weak coherent light L2 are made equal. Specifically, when the BPF is OFF, the NDF which reduces the intensity is used so that the weak coherent light L2 having an intensity $I_b$ which is lower than the maximum intensity $I_a$ of the partially coherent light L1 is emitted.

Figure 21:
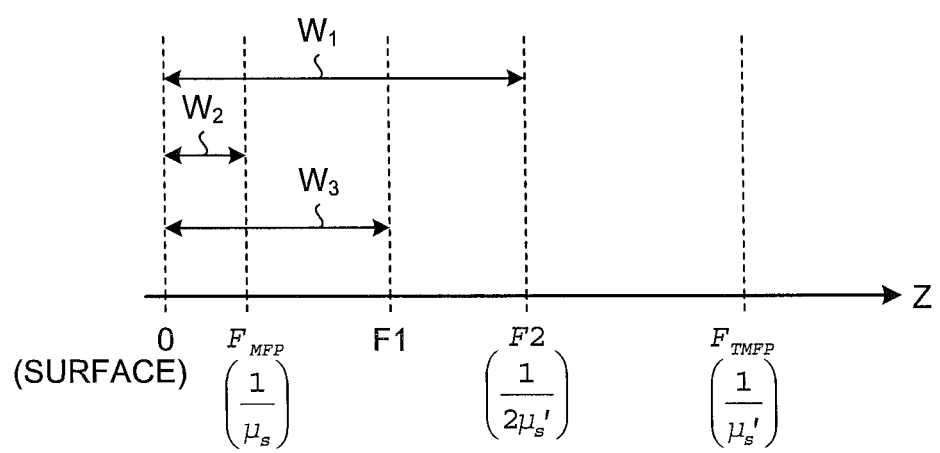
FIG. 21 is a schematic diagram illustrating variations in the coherence length of weak coherent light.

FIG. 21 is a schematic diagram illustrating variations in the coherence length of the weak coherent light. For example, as illustrated in FIG. 21, when partially coherent light having a coherence length $W_1$ corresponding to a depth F2 which corresponds to half the TMFP is emitted or weak coherent light having a coherence length $W_2$ corresponding to a depth $F_{MFP}$ which corresponds to the MFP is emitted, an interference component signal which is isolated from a base part including no scattered and returned light can be acquired in the calculation process in the interference component extracting unit 153. Further, when weak coherent light having a coherence length $W_3$ corresponding to a depth F1 which is deeper than the depth $F_{MFP}$ and shallower than the depth F2 is emitted, an interference component signal in which scattered and returned light scattered in an area from the surface to the depth F1 is also excluded can be acquired in the calculation process in the interference component extracting unit 153. Thus, it is also possible to acquire an interference component signal corresponding to a desired depth by adjusting the coherence length of the weak coherent light.

Figure 22:
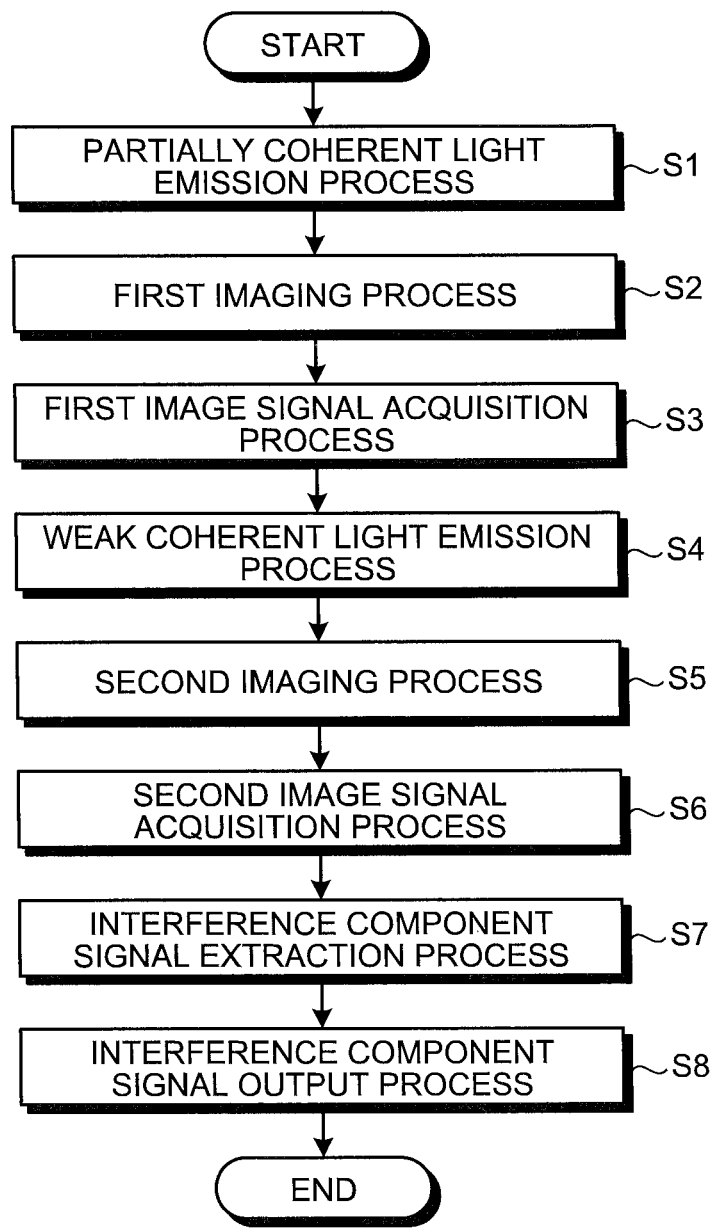
FIG. 22 is a flowchart illustrating a procedure for acquiring an interference component signal by the signal processing apparatus illustrated in FIG. 1.

Next, the process for acquiring an interference component signal by the signal processing apparatus 120 will be described. FIG. 22 is a flowchart illustrating a procedure for acquiring an interference component signal by the signal processing apparatus 120 illustrated in FIG. 1.

As illustrated in FIG. 22, the light source controller 152 first executes a partially coherent light emission process for causing the light source unit 121 to emit partially coherent light (step S1). In this case, the light source controller 152 causes the SLD 124 to emit broadband light and controls the controller 129 to cause the filter wheel 125 to dispose the BPF on the optical path. The control unit 151 performs a first imaging process for causing the image sensor 105 to capture an image of the detection area synchronously with the process of step S1 (step S2), and performs a first image signal acquisition process for acquiring a first image signal which is an image signal of the body tissue 100 irradiated with the partially coherent light through the signal output unit 106 (step S3).

The light source controller 152 executes a weak coherent light emission process for causing the light source 121 to emit weak coherent light (step S4). In this case, the light source controller 152 causes the SLD 124 to emit broadband light and causes the filter wheel 125 to dispose the NDF on the optical path through the controller 129. The control unit 151 performs a second imaging process for causing the image sensor 105 to capture an image of the detection area synchronously with the process of step S4 (step S5), and performs a second image signal acquisition process for acquiring a second image signal which is an image signal of the body tissue 100 irradiated with the weak coherent light through the signal output unit 106 (step S6).

The interference component extracting unit 153 performs an interference component signal extraction process for extracting an interference component signal by excluding a noninterference component from the signal of scattered and returned light on the basis of a subtraction image signal obtained by the image sensor 105 (step S7). Specifically, the interference component extracting unit 153 calculates the difference in corresponding parts between the first image signal and the second image signal respectively acquired in step S3 and step S6 to acquire a subtraction image signal as an interference component image signal.

Figure 23:
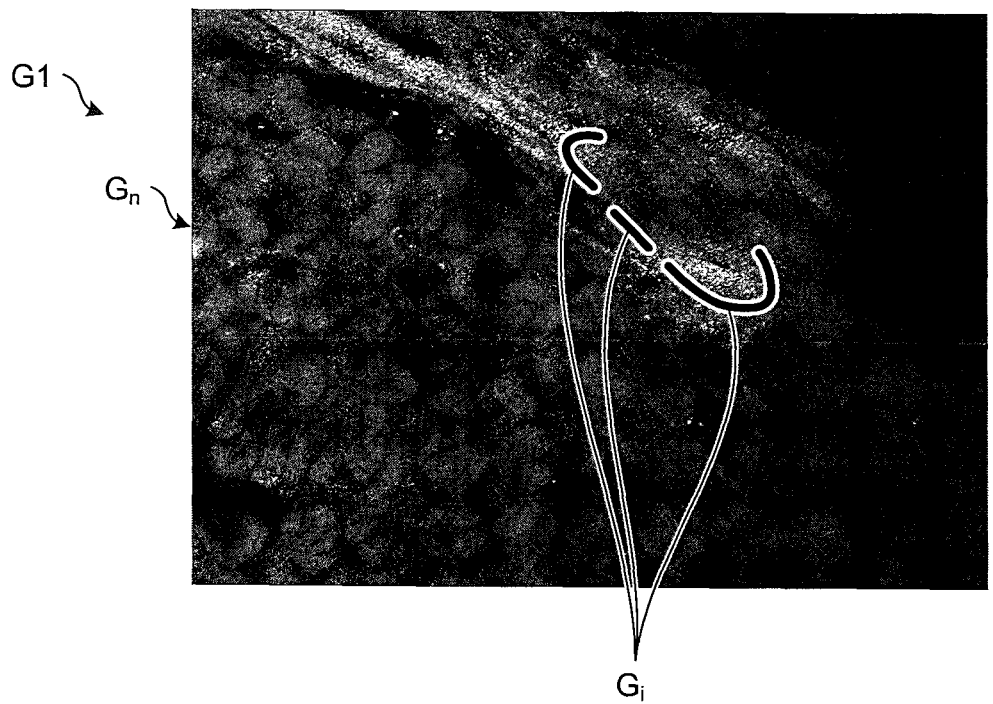
FIG. 23 is an example of an image which is displayed and output by a display device illustrated in FIG. 1.

The control unit 151 performs an interference component signal output process for causing the display device 190 to display and output information relating to the interference component signal extracted in step S7 (step S8). In the interference component signal output process, the interference component signal acquired in step S7 may be output as it is to the characteristic value calculation unit 154 or the display device 190. FIG. 23 is an example of an image which is displayed and output by the display device 190. As illustrated in FIG. 23, the control unit 151 may cause the display device 190 to display and output an image G1 which is obtained by superimposing a line image $G_i$ which represents a characteristic value relating to the properties of the body tissue 100, the characteristic value being calculated by the characteristic value calculation unit 154, for example, blood flow in a capillary vessel on a normal image $G_n$ which is captured during irradiation of observation light.

In this manner, according to the first embodiment, only an interference component based on scattered and returned light having been scattered and returned from the surface layer of a light scattering body is accurately acquired by emitting partially coherent light having a coherence length that is equal to or more than the inverse of the scattering coefficient of the body tissue 100 and shorter than half the inverse of the reduced scattering coefficient of the body tissue 100 and excluding a noninterference component from the intensity of scattered and returned light corresponding to the partially coherent light.

According to the first embodiment, only an interference component based on scattered and returned light that has been scattered and returned from the surface layer of a light scattering body is accurately acquired by emitting partially coherent light having a predefined coherence length for a scattering body of the same kind as the body tissue 100 to generate an interference component within an area corresponding to an intensity of 10% of the maximum intensity of scattered and returned light from the center point of a focused illumination area in an internally scattered and returned light distribution which is formed on the surface of the scattering body when focused illumination is performed on the scattering body and by excluding a noninterference component from the signal of scattered and returned light corresponding to the partially coherent light.

Further, according to the first embodiment, the intensity of returned light in emitting weak coherent light substantially corresponding to a noninterference component is detected in addition to the intensity of scattered and returned light in emitting the partially coherent light, and the difference in corresponding parts between the intensity of the scattered and returned light corresponding to the partially coherent light and the intensity of the scattered and returned light corresponding to the weak coherent light is calculated to extract an interference component. Thus, it is possible to appropriately acquire only an interference component based on scattered and returned light that has been scattered and returned from the surface layer of the light scattering body.

Further, the light source unit 121 is not limited to the combination of the SLD 124 and the filter wheel 125, and a current application method such as high frequency superimposing may be applied to a laser diode (LD) as long as the coherence length set value can be temporally switched by irradiation of partially coherent light and weak coherent light. Further, the light source unit 121 may have a configuration of the combination of an LD capable of performing high intensity output and an NDF. In this case, the LD may be lit with different intensities in step S1 and step S2 of FIG. 22, and the emitted light amount may be adjusted by the NDF in step S2 and step S5.

Figure 24:
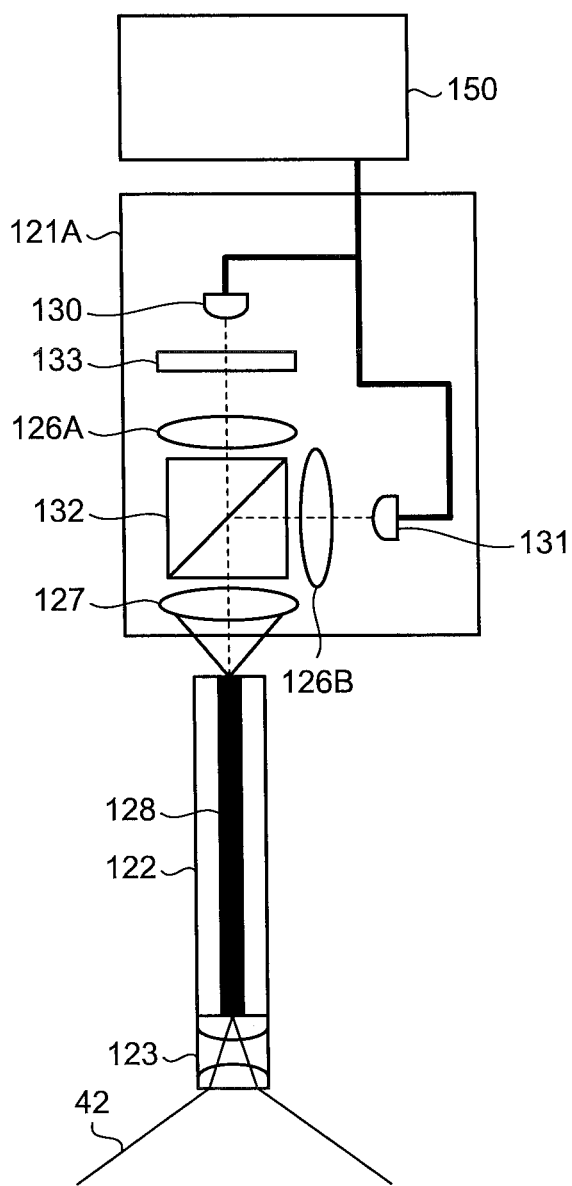
FIG. 24 is a diagram illustrating another example of the configuration of the light source unit illustrated in FIG. 1.

Further, in the first embodiment, a light source which emits weak coherent light may be provided separately from a light source which emits partially coherent light. FIG. 24 is a diagram illustrating another example of the configuration of the light source unit illustrated in FIG. 1 and also illustrates a principal part of the signal processing apparatus 120.

A light source unit 121A illustrated in FIG. 24 is provided with a partially coherent laser (first light source) 130 which emits partially coherent light with a coherence length satisfying the above condition, an LED (second light source) 131 which emits weak coherent light, a beam splitter 132, a beam profile shaping optical system 133 (light distribution adjusting unit), a collimator lens 126A which is disposed between the partially coherent laser 130 and the beam splitter 132, a collimator lens 126B which is disposed between the LED 131 and the beam splitter 132, and a focus lens 127. Note that the beam splitter 132 may be a dichroic mirror. The partially coherent laser 130 can be implemented by the above-described combination of the broadband light source, and a BPF and an NDF, or high frequency superimposing modulation driving of an LD element, or the combination of a high power LD and an NDF.

The light source controller 152 causes the partially coherent laser 130 to emit partially coherent light in step S1 illustrated in FIG. 22, and causes the LED 131 to emit weak coherent light in step S4. The light source controller 152 adjusts output of the partially coherent laser 130 and output of the LED 131 so that the total amount of the partially coherent light and the total amount of the weak coherent light are made equal. The beam profile shaping optical system 133 makes an adjustment so as that emitted light spatial distributions of the partially coherent light and the weak coherent light which are input to the beam splitter 132 are made equal. For example, the beam profile shaping optical system 133 aligns an irradiation angle of the partially coherent light emitted from the partially coherent laser 130 with an irradiation angle of the weak coherent light emitted from the LED 131. Although, in FIG. 24, the beam profile shaping optical system 133 is disposed with respect to the partially coherent laser 130, the beam profile shaping optical system 133 may be disposed with respect to the LED 131 and may align the irradiation angle of the weak coherent light emitted from the LED 131 with the irradiation angle of the partially coherent light emitted from the partially coherent laser 130.

Figure 25:
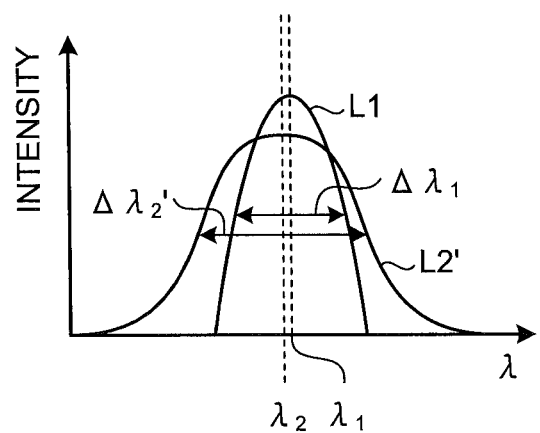
FIG. 25 is a diagram illustrating wavelength dependence of the intensity of partially coherent light emitted by a partially coherent laser illustrated in FIG. 24 and wavelength dependence of the intensity of weak coherent light emitted by an LED illustrated in FIG. 24.

FIG. 25 is a diagram illustrating wavelength dependence of the intensity of partially coherent light emitted by the partially coherent laser 130 and wavelength dependence of the intensity of weak coherent light emitted by the LED 131. As illustrated in FIG. 25, when the configuration of the light source unit 121A is employed, a center wavelength $\lambda_1$ of partially coherent light L1 and a center wavelength $\lambda_2$ of weak coherent light L2' may not necessarily agree with each other. In the example of FIG. 25, the wavelength band of a full width at half maximum $\Delta\lambda_2'$ of the weak coherent light includes the wavelength band of a full width at half maximum $\Delta\lambda_1$ of the other partially coherent light, and an interference component can be extracted by the interference component extracting unit 153. Further, an interference component can be extracted by the interference component extracting unit 153 when at least an overlap with the center wavelength of a part of the other light exists. Thus, it is not required that the entire wavelength band of the full width at half maximum $\Delta\lambda_1$ of the other partially coherent light be included in the wavelength band of the full width at half maximum $\Delta\lambda_2'$ of the weak coherent light.

Figure 26:
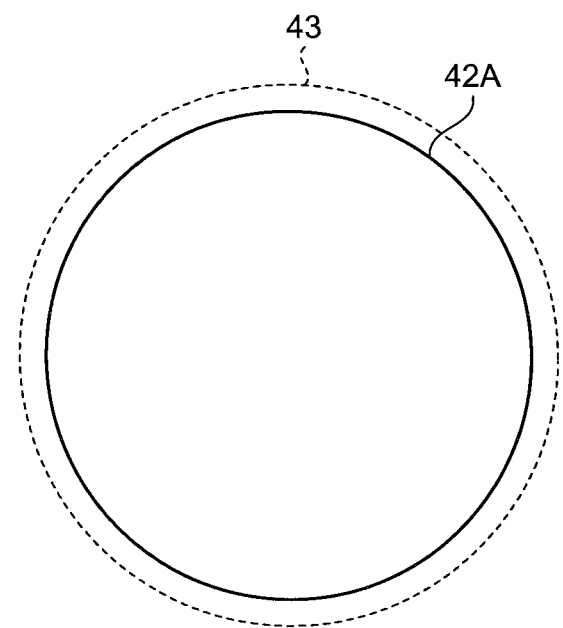
FIG. 26 is a diagram illustrating an example of an observation area of an endoscope apparatus and an illumination area of the signal processing apparatus.
Figure 27:
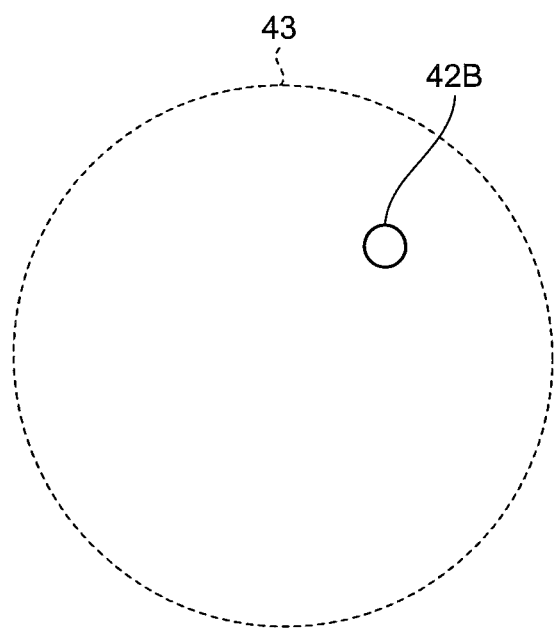
FIG. 27 is a diagram illustrating an example of the observation area of the endoscope apparatus and the illumination area of the signal processing apparatus.
Figure 28:
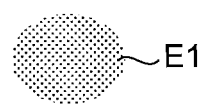
FIG. 28 is a diagram illustrating an example of a light irradiation area on a body tissue by the signal processing apparatus illustrated in FIG. 1.
Figure 29:
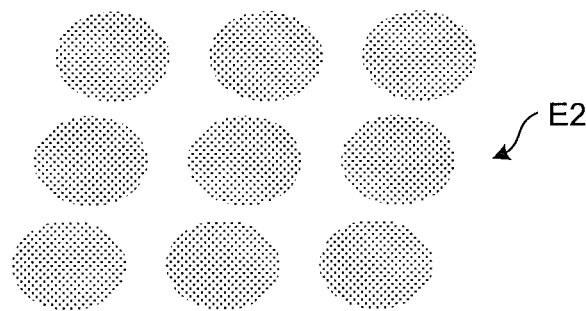
FIG. 29 is a diagram illustrating an example of the light irradiation area on the body tissue by the signal processing apparatus illustrated in FIG. 1.
Figure 30:
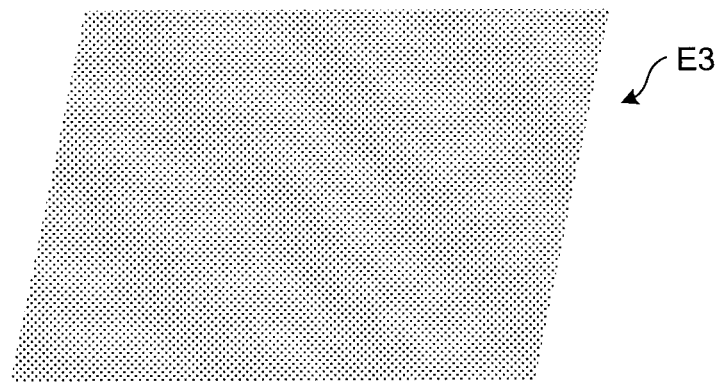
FIG. 30 is a diagram illustrating an example of the light irradiation area on the body tissue by the signal processing apparatus illustrated in FIG. 1.
Figure 31:
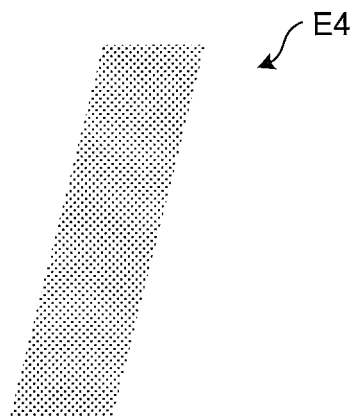
FIG. 31 is a diagram illustrating an example of the light irradiation area on the body tissue by the signal processing apparatus illustrated in FIG. 1.
Figure 32:
FIG. 32 is a diagram illustrating an example of the light irradiation area on the body tissue by the signal processing apparatus illustrated in FIG. 1.
Figure 33:
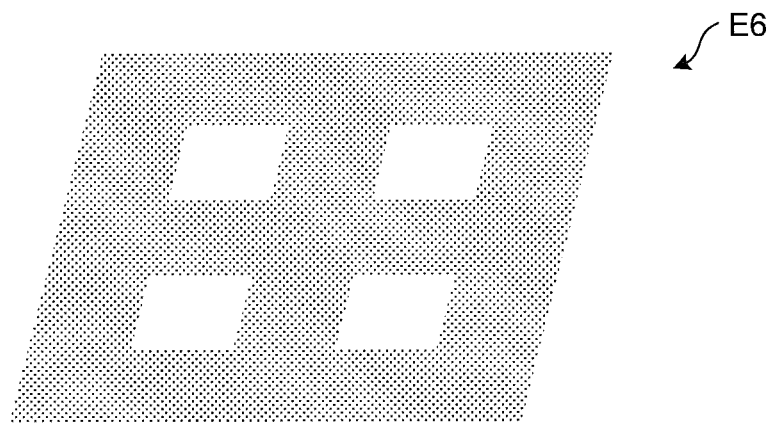
FIG. 33 is a diagram illustrating an example of the light irradiation area on the body tissue by the signal processing apparatus illustrated in FIG. 1.

Further, FIGS. 26 and 27 illustrate examples of the observation area 43 of the endoscope apparatus 101 and the illumination area 42 of the signal processing apparatus 120. The illumination area 42, that is, an interference component acquisition target area by the signal processing apparatus 120 may be an area 42A which has a size substantially equal to the size of the observation area 43 or may be a spot area 42B which is smaller than the observation area 43 as illustrated in FIG. 27. The same applies to second to sixth embodiments described below.

FIGS. 28 to 33 are diagrams illustrating examples of a light irradiation area on the body tissue 100 by the signal processing apparatus 120. The signal processing apparatus 120 may apply not only a single spot light beam E1 (refer to FIG. 28), but also a plurality of spot light beams E2 which do not overlap each other (refer to FIG. 29) or a uniform illumination light beam E3 which is capable of uniformly illuminating the inside of a predetermined area (refer to FIG. 30) to the surface of the body tissue 100. Further, the signal processing apparatus 120 may apply not only a spot light beam, but also one line-shaped light beam E4 or a plurality of line-shaped light beams E5 (refer to FIGS. 31 and 32) or a grid-like light beam E6 (refer to FIG. 33). The same applies to the second to sixth embodiments described below.

Second Embodiment

Figure 34:
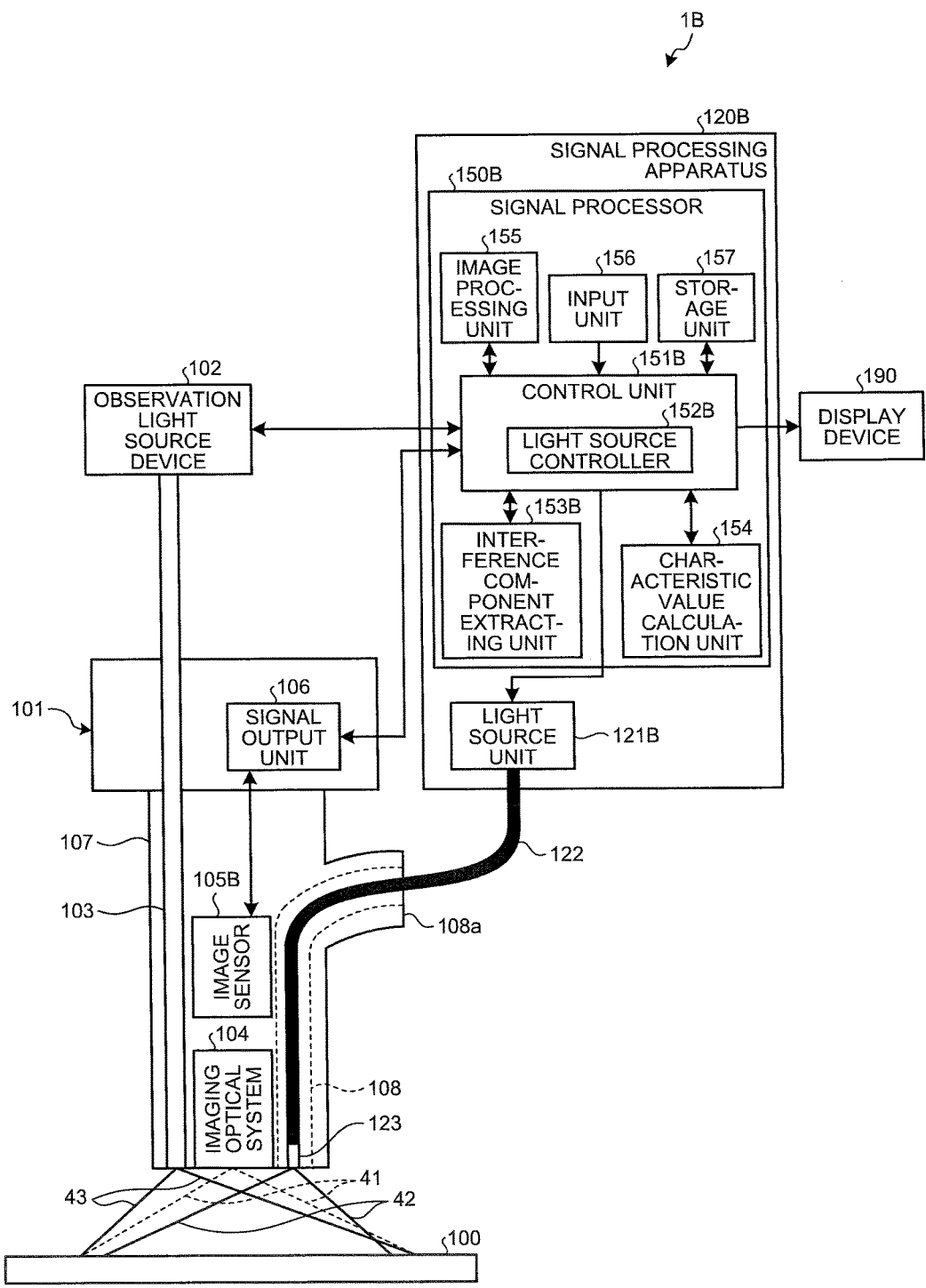
FIG. 34 is a diagram illustrating a schematic configuration of an endoscope system according to a second embodiment of the present invention.

Next, a second embodiment will be described. FIG. 34 is a diagram illustrating a schematic configuration of an endoscope system according to the second embodiment of the present invention.

As illustrated in FIG. 34, an endoscope system 1B according to the second embodiment is provided with an image sensor 105B and a signal processing apparatus 120B as compared with the endoscope system 1 illustrated in FIG. 1. The image sensor 105B disperses light into wavelength band light corresponding to partially coherent light and wavelength band light corresponding to weak coherent light at an input stage of a light receiving unit. The signal processing apparatus 120B is provided with a light source unit 121B which emits partially coherent light and weak coherent light having a full width at half maximum wavelength band which does not overlap a full width at half maximum wavelength band of the partially coherent light, a control unit 151B which includes a light source controller 152B which causes the light source unit 121B to synchronously emit the partially coherent light and the weak coherent light, and a signal processor 150B which includes an interference component extracting unit 153B which separates an image signal corresponding to the partially coherent light and an image signal corresponding to the weak coherent light from an image signal captured by the image sensor 105B and calculates the difference in corresponding parts between the two separated image signals to extract an interference component signal.

Figure 35:
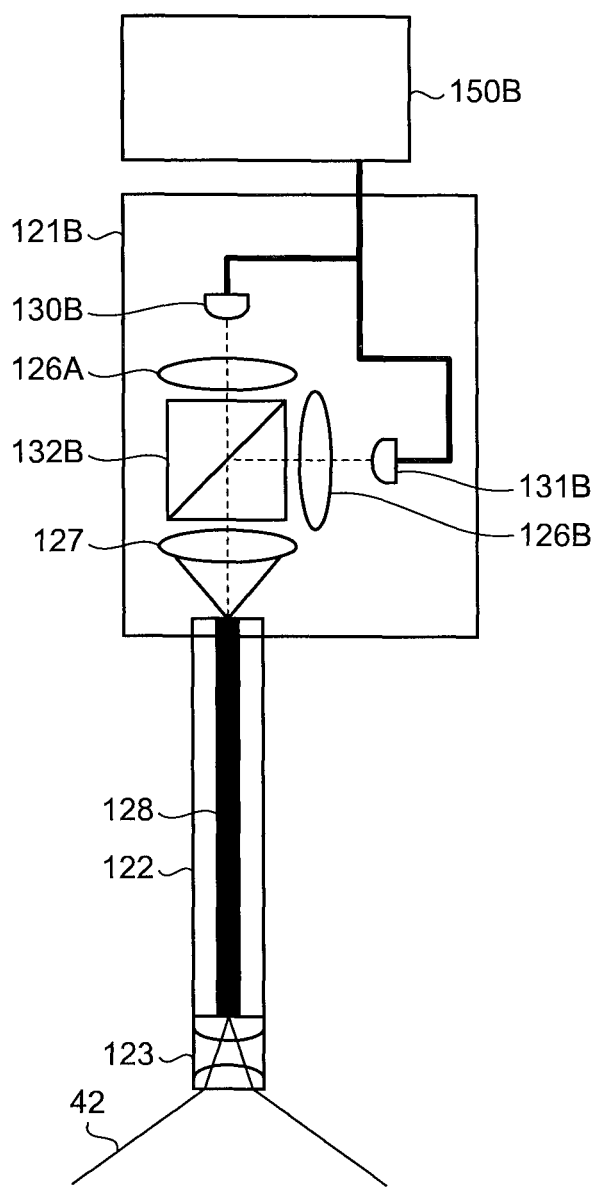
FIG. 35 is a diagram illustrating the configuration of a principal part of a signal processing apparatus including a light source unit illustrated in FIG. 34.

FIG. 35 is a diagram illustrating the configuration of a principal part of the signal processing apparatus 120B including the light source unit 121B. As illustrated in FIG. 35, the light source unit 121B is provided with a partially coherent laser 130B which emits partially coherent light with a coherence length satisfying the condition described in the first embodiment, an LED 131B which emits weak coherent light, a beam splitter 132B, a collimator lens 126A which is disposed between the partially coherent laser 130B and the beam splitter 132B, a collimator lens 126B which is disposed between the LED 131B and the beam splitter 132B, and a focus lens 127. Note that the beam splitter 132B may be a dichroic mirror.

Figure 36:
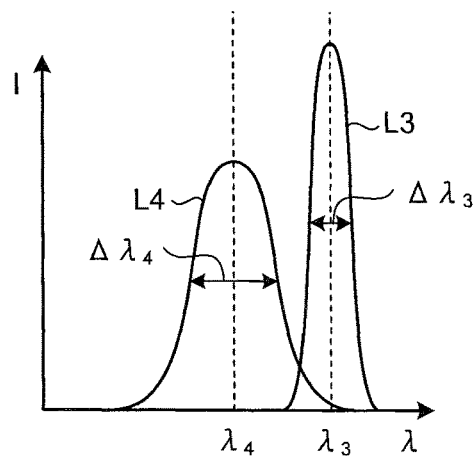
FIG. 36 is a diagram illustrating wavelength dependence of the intensity of partially coherent light emitted by a partially coherent laser illustrated in FIG. 35 and wavelength dependence of the intensity of weak coherent light emitted by an LED illustrated in FIG. 35.

FIG. 36 is a diagram illustrating wavelength dependence of the intensity of partially coherent light emitted by the partially coherent laser 130B and wavelength dependence of the intensity of weak coherent light emitted by the LED 131B.

As illustrated in FIG. 36, the partially coherent laser 130B emits partially coherent light L3 which has a center wavelength $\lambda_3$, a full width at half maximum $\Delta\lambda_3$, and a coherence length $L_c$ satisfying the condition described in the first embodiment. The LED 131B emits weak coherent light L4 which has a center wavelength $\lambda_4$ and a full width at half maximum $\Delta\lambda_4$. The full width at half maximum wavelength band of the partially coherent light L3 and the full width at half maximum wavelength band of the weak coherent light L4 do not overlap each other. Thus, the partially coherent light L3 and the weak coherent light L4 can be obtained by dispersion in the image sensor 105B (described below). Further, similarly to the first embodiment, the total amount of the partially coherent light L3 and the total amount of the weak coherent light L4 are equal. The light source controller 152B causes the partially coherent laser 130B and the LED 131B to synchronously emit the partially coherent light L3 and the weak coherent light L4.

Figure 37:
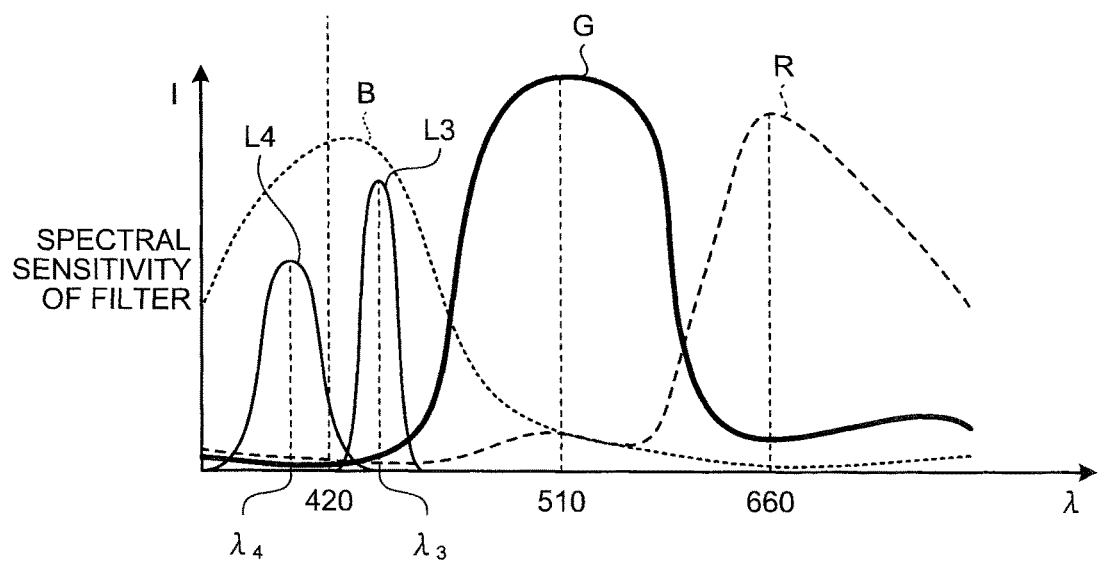
FIG. 37 is a diagram illustrating the spectral sensitivities in filters which are included in an image sensor in the second embodiment.

FIG. 37 is a diagram illustrating the spectral sensitivities in filters which are included in the image sensor 105B (described below). In FIG. 37, in contrast with the filters actually included in the image sensor 105B, the spectral sensitivities of red (R), green (G), and blue (B) filters which are included in a common image sensor will also be described. In a common image sensor, as illustrated in FIG. 37, the R filter passes light having a wavelength band of 600 nm to 700 nm, the G filter passes light having a wavelength band of 500 nm to 600 nm, and the B filter passes light having a wavelength band of 400 nm to 500 nm. As illustrated in FIG. 37, the wavelength band of the partially coherent light L3 and the wavelength band of the weak coherent light L4 are included in the wavelength band of 400 nm to 500 nm in which the B filter has a spectral sensitivity.

Figure 38:
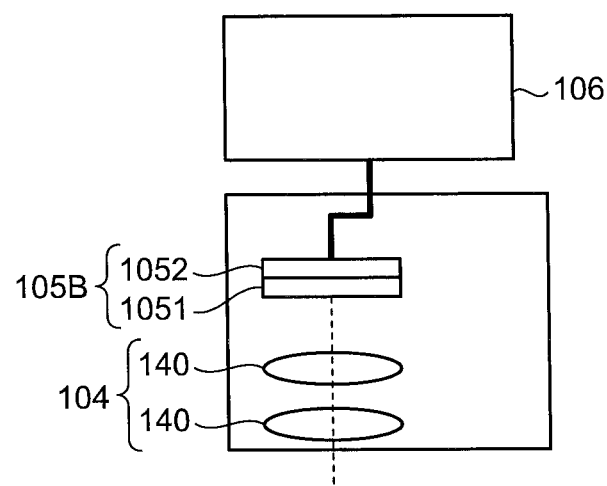
FIG. 38 is a diagram illustrating the configuration of an imaging optical system and the image sensor illustrated in FIG. 34.

FIG. 38 is a diagram illustrating the configuration of an imaging optical system 104 and the image sensor 105B illustrated in FIG. 34. FIG. 38 also illustrates a signal output unit 106. As illustrated in FIG. 38, the imaging optical system 104 includes a plurality of lenses 140. The image sensor 105B includes a light receiving unit 1052 and a filter group 1051 (spectral unit) disposed at the input stage of the light receiving unit 1052.

Figure 39:
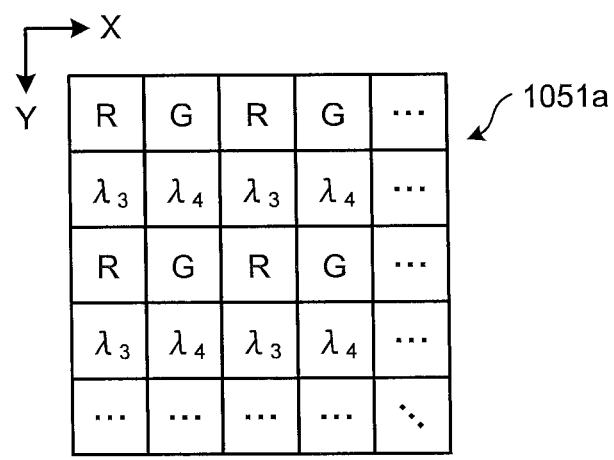
FIG. 39 is a diagram illustrating a filter array of a filter group illustrated in FIG. 38.

FIG. 39 is a diagram illustrating a filter array of the filter group 1051 illustrated in FIG. 38. As represented by an array 1051a of FIG. 39, the filter group 1051 employs a Bayer array which corresponds to an array of a pixel group in the light receiving unit 1052. In each even row, $\lambda_3$ filters each of which passes only light having the center wavelength $\lambda_3$ and the wavelength band of the full width at half maximum $\Delta\lambda_3$ and $\lambda_4$ filters each of which passes only light having the center wavelength $\lambda_4$ and the wavelength band of the full width at half maximum $\Delta\lambda_4$ are alternately arrayed in the horizontal direction. In each odd row, R filters and G filters are alternately arrayed in the horizontal direction. In this manner, the filter group 1051 has a function of separating light having a wavelength band corresponding to the partially coherent light and light having a wavelength band corresponding to the weak coherent light. In the filter array 1051a, the spectral sensitivity of the $\lambda_4$ filter and the spectral sensitivity of the $\lambda_3$ filter are set so that an integrated intensity of the partially coherent light and an integrated intensity of the weak coherent light are made equal in order to obtain the partially coherent light and the weak coherent light.

During simultaneous emission of the partially coherent light and the weak coherent light in the light source unit 121B, the interference component extracting unit 153B performs an interference component extraction process after separating an output signal by a pixel that receives light passed through the $\lambda_3$ filter in the even column of the array 1051a as a first image signal corresponding to the partially coherent light and separating an output signal by a pixel that receives light passed through the $\lambda_4$ filter as a second image signal corresponding to the weak coherent light. During normal observation, the image processing unit 155 performs each image processing with an output signal by a pixel that receives light passed through each of the $\lambda_3$ and $\lambda_4$ filters in the even row of the array 1051a as a B image signal. Further, the image processing unit 155 performs image processing with an output signal by a pixel that receives light passed through the R filter in the odd row of the array 1051a as an R image signal and an output signal by a pixel that receives light passed through the G filter in the odd row as a G image signal.

Figure 40:
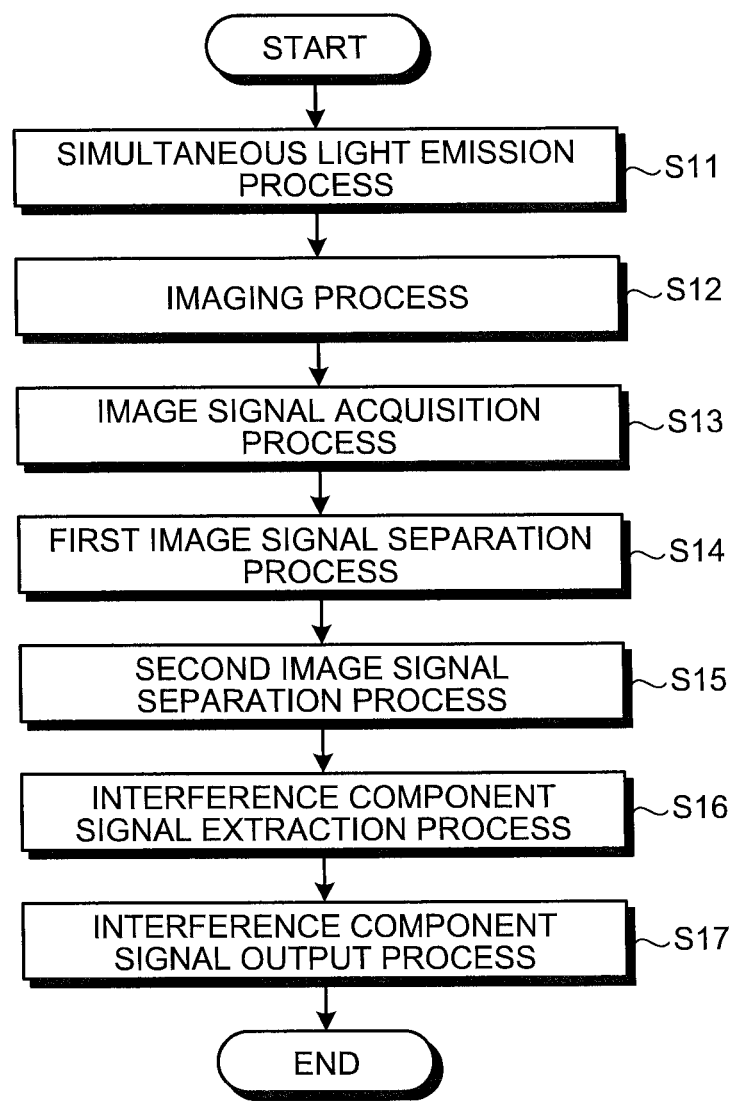
FIG. 40 is a flowchart illustrating a procedure for acquiring an interference component signal by the signal processing apparatus illustrated in FIG. 34.

FIG. 40 is a flowchart illustrating a procedure for acquiring an interference component signal by the signal processing apparatus 120B illustrated in FIG. 34. As illustrated in FIG. 40, the light source controller 152B first executes a simultaneous light emission process for causing the light source 121B to simultaneously emit partially coherent light and weak coherent light (step S11). The control unit 151B performs an imaging process for causing the image sensor 105B to capture an image of a detection area synchronously with the process of step S11 (step S12), and performs an image signal acquisition process for acquiring an image signal through the signal output unit 106 (step S13).

The interference component extracting unit 153B performs a first image signal separation process for separating an output signal by a pixel that receives light passed through the $\lambda_3$ filter from an image signal output from the image sensor 105B as a first image signal corresponding to the partially coherent light (step S14). The interference component extracting unit 153B performs a second image signal separation process for separating an output signal by a pixel that receives light passed through the $\lambda_4$ filter from the same image signal output from the image sensor 105B as a second image signal corresponding to the weak coherent light (step S15). The interference component extracting unit 153B performs an interference component signal extraction process for calculating the difference in corresponding parts between the first image signal and the second image signal and acquiring a subtraction image signal as an interference component image signal (step S16). Step S17 corresponds to step S8 illustrated in FIG. 22.

Also when partially coherent light and weak coherent light are simultaneously emitted as in the second embodiment, the intensity of scattered and returned light in emitting the partially coherent light is separated from the intensity of scattered and returned light in emitting the weak coherent light substantially corresponding to a noninterference component, and the difference between the intensity of the scattered and returned light corresponding to the partially coherent light and the intensity of the scattered and returned light corresponding to the weak coherent light is calculated to extract an interference component. Thus, similarly to the first embodiment, it is possible to appropriately acquire only an interference component based on scattered and returned light that has been scattered and returned from the surface layer of a light scattering body.

Figure 41:
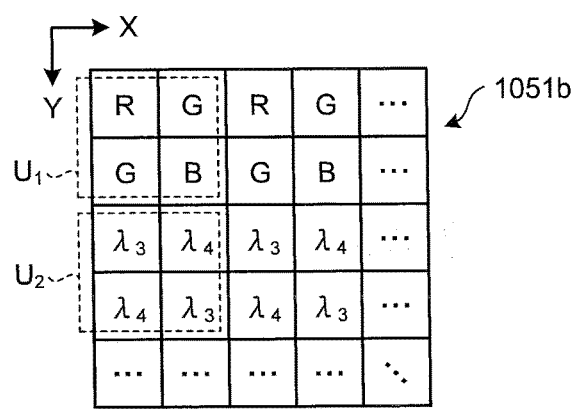
FIG. 41 is a diagram illustrating another example of the filter array of the filter group illustrated in FIG. 38.

Note that the array of the filter group 1051 of the image sensor 105B is not limited to the array 1051a of FIG. 39. FIG. 41 is a diagram illustrating another example of the filter array of the filter group 1051 illustrated in FIG. 38. As with an array 1051b illustrated in FIG. 41, two horizontal lines in which a plurality of filter units $U_1$ each of which includes R, G, G, and B filters are arranged in the horizontal direction and two horizontal lines in which a plurality of filter units $U_2$ each of which includes $\lambda_3$, $\lambda_4$, $\lambda_4$, and $\lambda_3$ filters are arranged in the horizontal direction may be alternately arranged. In addition to the array 1051b, the filter units $U_1$ and the filter units $U_2$ may be alternately arranged in the horizontal direction.

Figure 42:
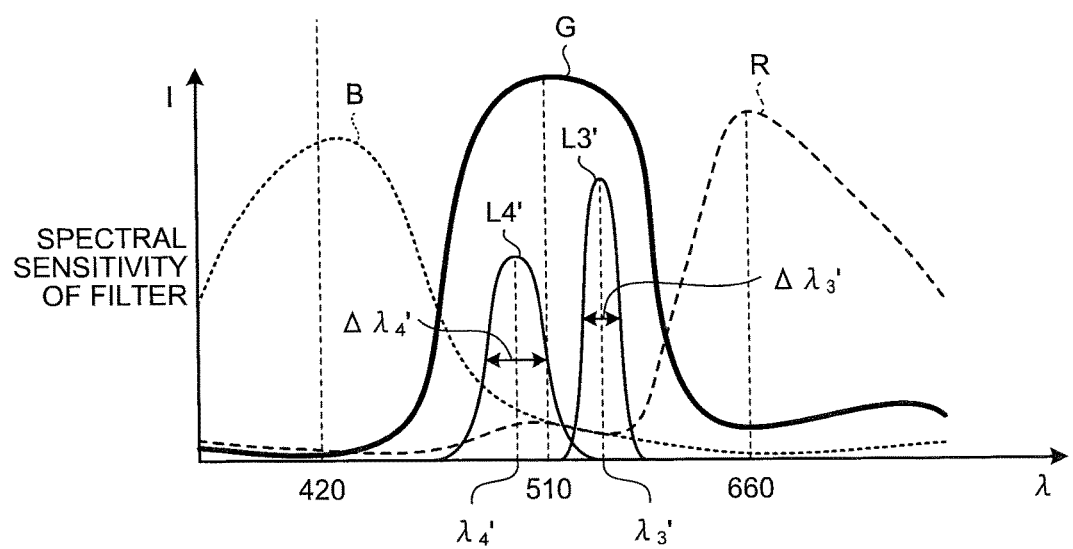
FIG. 42 is a diagram illustrating wavelength dependence of the intensity of another partially coherent light emitted by the partially coherent laser in the light source unit illustrated in FIG. 35 and wavelength dependence of the intensity of another weak coherent light emitted by the LED in the light source unit.

Further, FIG. 42 is a diagram illustrating wavelength dependence of the intensity of another partially coherent light emitted by the partially coherent laser 130B in the light source unit 121B and wavelength dependence of the intensity of another weak coherent light emitted by the LED 131B in the light source unit 121B. As illustrated in FIG. 42, the partially coherent laser 130B may emit partially coherent light L3' which has a full width at half maximum $\Delta\lambda_3$' included in the wavelength band of 500 nm to 600 nm in which the G filter has a spectral sensitivity and a center wavelength $\lambda_3$'. Further, the LED 131B may emit weak coherent light L4' which has a full width at half maximum $\Delta\lambda_4$' included in the wavelength band of 500 nm to 600 nm in which the G filter has a spectral sensitivity and a center wavelength $\lambda_4$'.

Figures 43, 44:
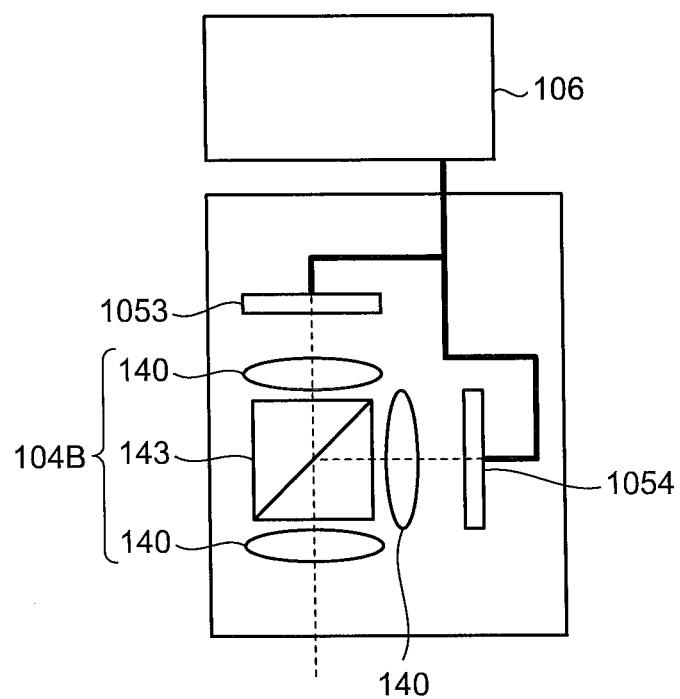
FIG. 43 is a diagram illustrating another example of the filter array of the filter group illustrated in FIG. 38.
FIG. 44 is a diagram illustrating another configuration of the imaging optical system and the image sensor illustrated in FIG. 38.

FIG. 43 is a diagram illustrating another example of the filter array of the filter group 1051. An array 1051c illustrated in FIG. 43 has a configuration in which R filters and $\lambda_3$' filters each of which passes only light having the center wavelength $\lambda_3$' and the wavelength band $\Delta\lambda_3$' are alternately arrayed in the horizontal direction in each odd row of the Bayer array, and $\lambda_4$' filters each of which passes only light having the center wavelength $\lambda_4$' and the wavelength band $\Delta\lambda_4$' and B filters are alternately arrayed in the horizontal direction in each even row. During simultaneous emission of the partially coherent light L3' and the weak coherent light L4' in the light source unit 121B, the interference component extracting unit 153B performs an interference component extraction process after separating an output signal by a pixel that receives light passed through the $\lambda_3$' filter in the odd row of the array 1051c as a first image signal corresponding to the partially coherent light L3' and separating an output signal by a pixel that receives light passed through the $\lambda_4$' filter in the even row of the array 1051c as a second image signal corresponding to the weak coherent light.

FIG. 44 is a diagram illustrating another configuration of the imaging optical system and the image sensor illustrated in FIG. 38. As illustrated in FIG. 44, a first image sensor 1053 and a second image sensor 1054 may be provided, and a dichroic mirror 143 may be provided in an imaging optical system 104B disposed at an input stage of each of the image sensors. Each of the first image sensor 1053 and the second image sensor 1054 is provided with a light receiving unit, a readout unit, and an AFE unit. The first image sensor 1053 further includes a color filter group which includes R, G, B filters arranged in the Bayer array at an input stage of the light receiving unit. The dichroic mirror 143 splits incident light returned from the body tissue 100 into wavelength band light corresponding to the partially coherent light L3 and wavelength band light corresponding to the weak coherent light L4.

Figure 45:
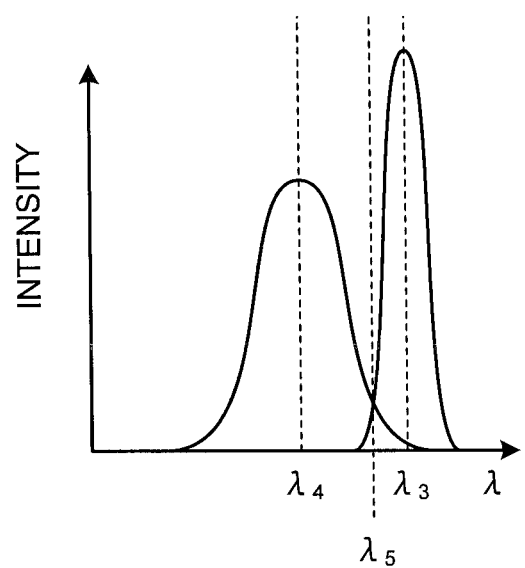
FIG. 45 is a schematic diagram illustrating wavelength separation by a dichroic mirror illustrated in FIG. 44.

FIG. 45 is a schematic diagram illustrating wavelength separation by the dichroic mirror 143 illustrated in FIG. 44. The dichroic mirror 143 splits incident light into two light beams at a wavelength $\lambda_5$ ($\lambda_3 < \lambda_5 < \lambda_4$) as a boundary. The dichroic mirror 143 transmits only incident light having a wavelength longer than the wavelength $\lambda_5$ to the back face thereof. Light having a wavelength longer than the wavelength $\lambda_5$ which is split from the incident light by the dichroic mirror 143 is received by the first image sensor 1053 which is located at the back face side of the dichroic mirror 143. Further, light having a wavelength shorter than the wavelength $\lambda_5$ which is split from the incident light by the dichroic mirror 143 is reflected by a reflection surface of the dichroic mirror 143 and received by the second image sensor 1054. During simultaneous emission of the partially coherent light L3 and the weak coherent light L4 in the light source unit 121B, the interference component extracting unit 153B acquires an image signal captured by the first image sensor 1053 as a first image signal corresponding to the partially coherent light L3 and acquires an image signal captured by the second image sensor 1054 as a second image signal corresponding to the weak coherent light L4, and performs an interference component extraction process. Further, during normal observation, the image processing unit 155 performs each image processing using an image signal captured by the first image sensor 1053.

Third Embodiment

Figure 46:
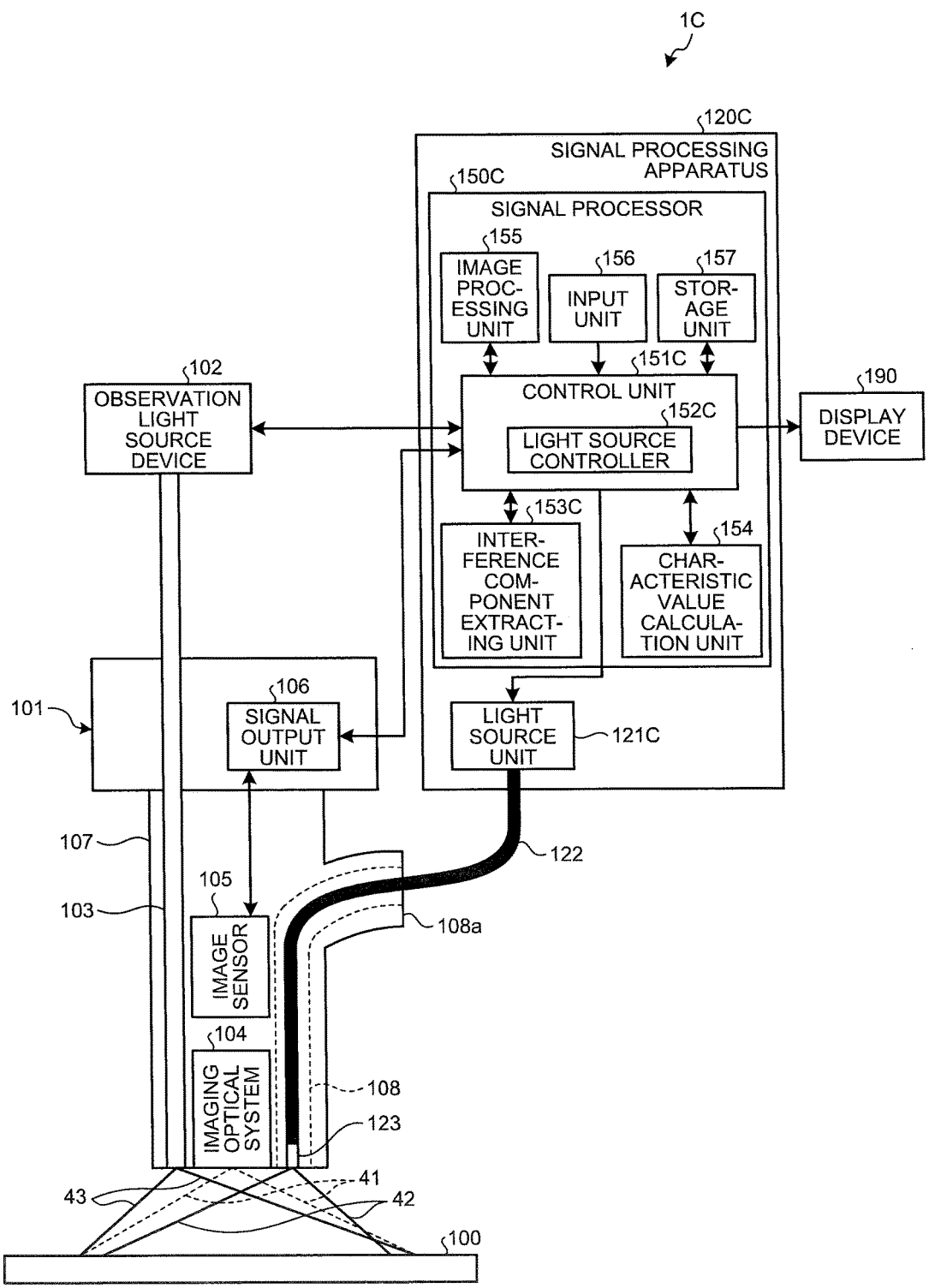
FIG. 46 is a diagram illustrating a schematic configuration of an endoscope system according to a third embodiment of the present invention.

Next, a third embodiment will be described. FIG. 46 is a diagram illustrating a schematic configuration of an endoscope system according to the third embodiment of the present invention.

Figure 47:
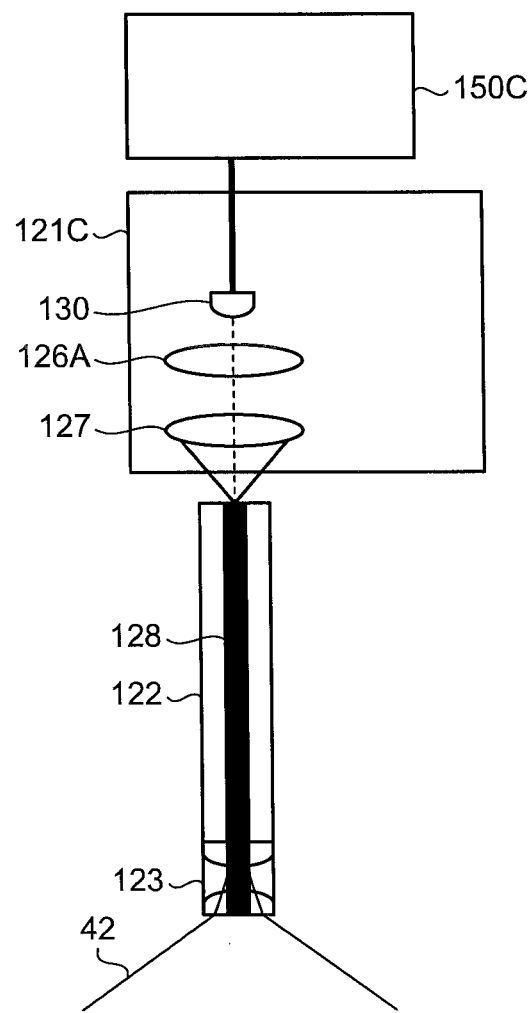
FIG. 47 is a diagram illustrating the configuration of a principal part of a signal processing apparatus including a light source unit illustrated in FIG. 46.

As illustrated in FIG. 46, an endoscope system 1C according to the third embodiment is provided with a signal processing apparatus 120C which includes a light source unit 121C and a signal processor 150C as compared with the endoscope system 1 illustrated in FIG. 1. FIG. 47 is a diagram illustrating the configuration of a principal part of the signal processing apparatus 120C including the light source unit 121C. As illustrated in FIG. 47, the light source unit 121C has a configuration in which the LED 131, the beam splitter 132, and the beam profile shaping optical system 133 are eliminated from the light source unit 121A illustrated in FIG. 24. The light source unit 121C emits only partially coherent light L1. A control unit 151C has a function similar to the function of the control unit 151 and includes a light source controller 152C which controls a partially coherent laser 130 of the light source unit 121C. An interference component extracting unit 153C acquires an image signal which is captured by an image sensor 105 during emission of the partially coherent light L1 in the light source unit 121C and subtracts the intensity of a noninterference component signal which is predefined from an image signal corresponding to the intensity of scattered and returned light to extract an interference component. For example, a median filter signal corresponding to the image signal captured by the image sensor 105 is used as a signal indicating the intensity of the noninterference component which is predefined.

Figure 48:
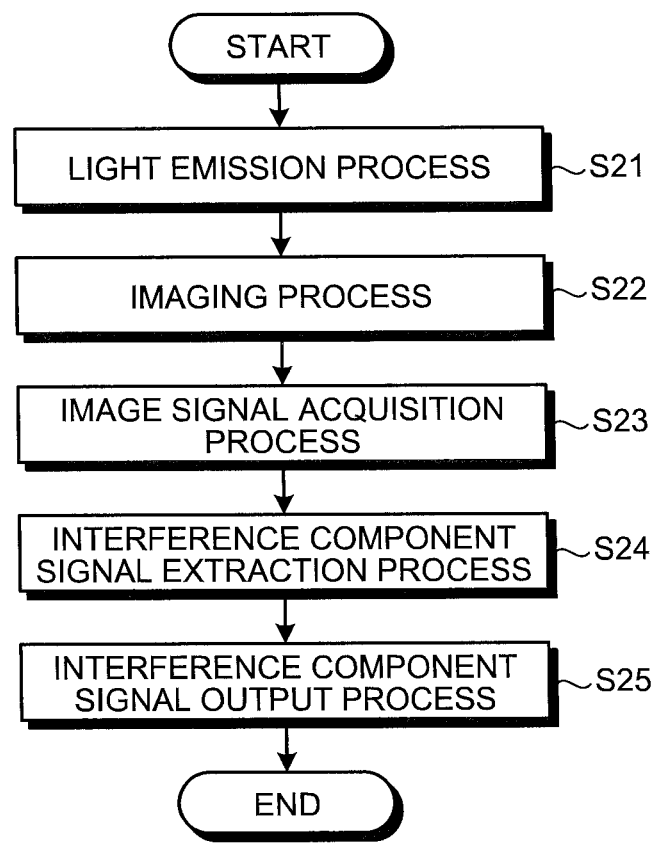
FIG. 48 is a flowchart illustrating a procedure for acquiring an interference component signal by the signal processing apparatus illustrated in FIG. 46.

FIG. 48 is a flowchart illustrating a procedure for acquiring an interference component signal by the signal processing apparatus 120C illustrated in FIG. 46. As illustrated in FIG. 48, the light source controller 152C first executes a light emission process for causing the light source 121C to emit partially coherent light (step S21). The control unit 151C performs an imaging process for causing the image sensor 105 to capture an image of a detection area synchronously with the process of step S21 (step S22), and performs an image signal acquisition process for acquiring an image signal through a signal output unit 106 (step S23).

The interference component extracting unit 153C performs an interference component signal extraction process for performing subtraction between an image signal output from the image sensor 105 and a median filter signal corresponding to the image signal in corresponding parts and extracting a subtraction image signal as an interference component signal (step S24). Step S25 corresponds to step S8 illustrated in FIG. 22.

As performed in the third embodiment, it is also possible to extract only an interference component from the intensity of scattered and returned light corresponding to the partially coherent light using a noninterference component signal having a predefined noninterference component.

Fourth Embodiment

Figure 49:
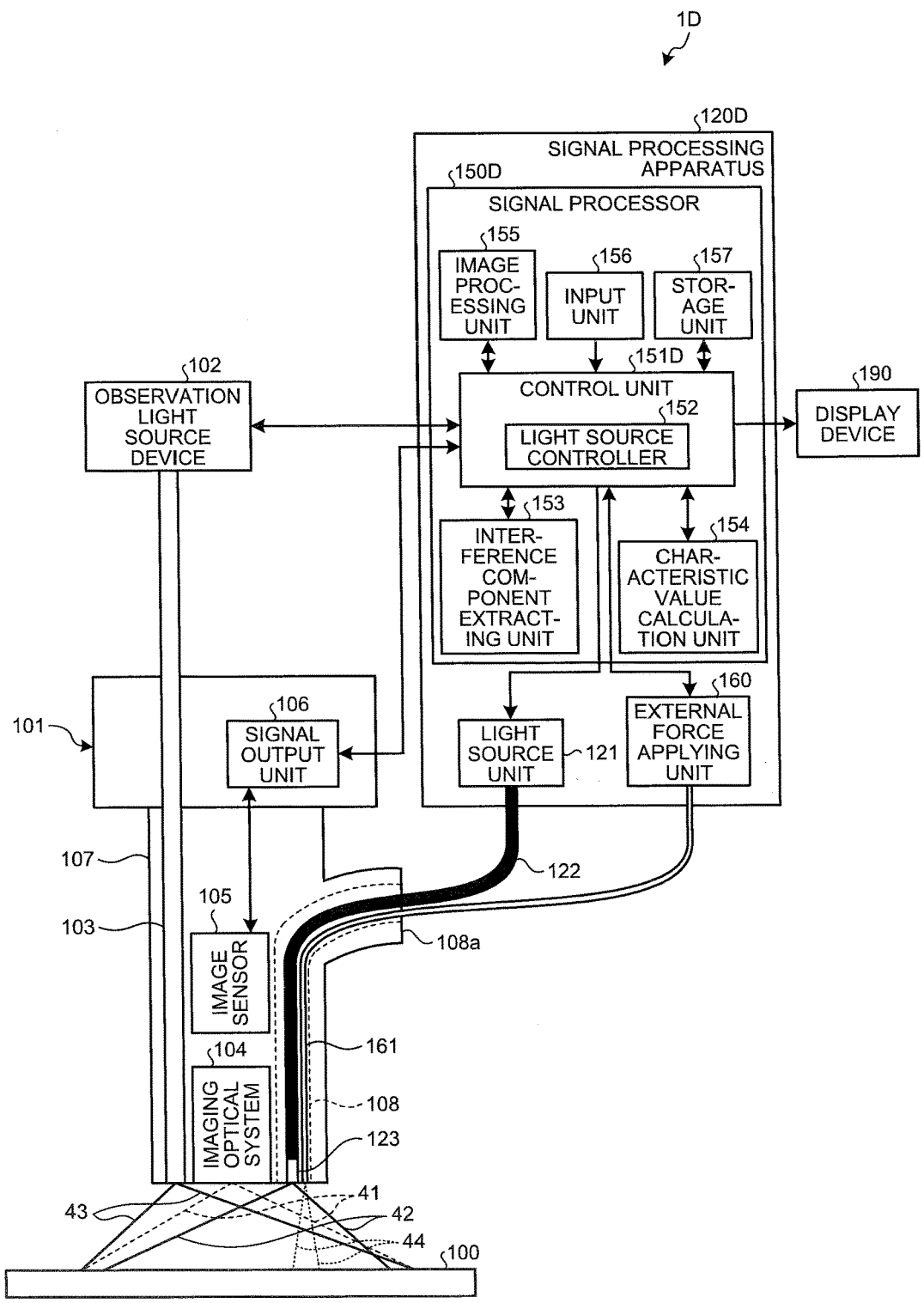
FIG. 49 is a diagram illustrating a schematic configuration of an endoscope system according to a fourth embodiment of the present invention.

Next, a fourth embodiment will be described. FIG. 49 is a diagram illustrating a schematic configuration of an endoscope system according to the fourth embodiment of the present invention.

As illustrated in FIG. 49, an endoscope system 1D according to the fourth embodiment includes a signal processing apparatus 120D which is further provided with an external force applying unit 160 in a signal processor 150D as compared with the endoscope system 1 illustrated in FIG. 1. The external force applying unit 160 has a function of applying external force which contactlessly deforms the surface of a body tissue 100 which is a light scattering body. The external force applying unit 160 generates, for example, wind pressure or acoustic radiation pressure as external force and outputs the generated external force to the surface of the body tissue 100 through a transmission path 161 which is disposed in such a manner that the distal end thereof reaches an opening on the distal end of an endoscope apparatus 101 through a treatment tool channel 108. An output range 44 of external force by the external force applying unit 160 is set inside an illumination area 42 and a detection area 41. Further, a control unit 151D in the signal processor 150D has a function similar to the function of the control unit 151 and also controls the external force applying unit 160.

Figure 50:
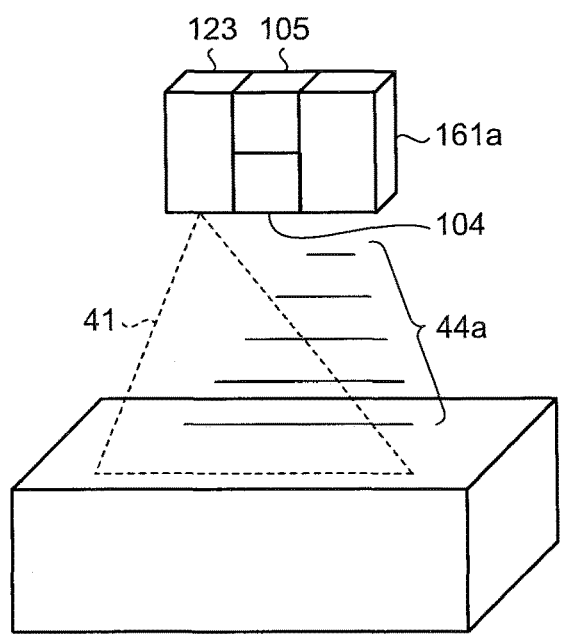
FIG. 50 is a schematic diagram illustrating an external force application process by an external force applying unit illustrated in FIG. 49.
Figure 51:
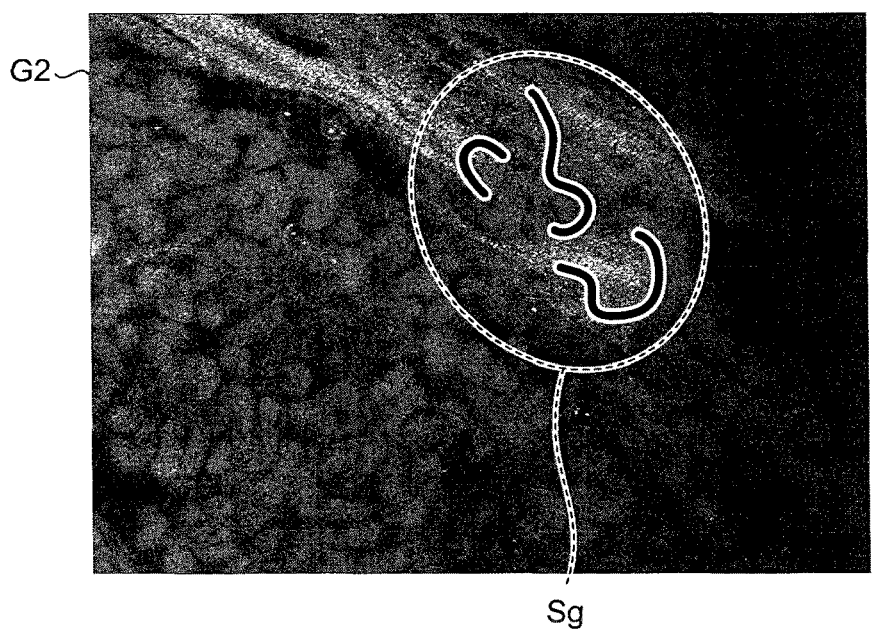
FIG. 51 is an example of an image which is displayed and output by a display device illustrated in FIG. 49.
Figure 52:
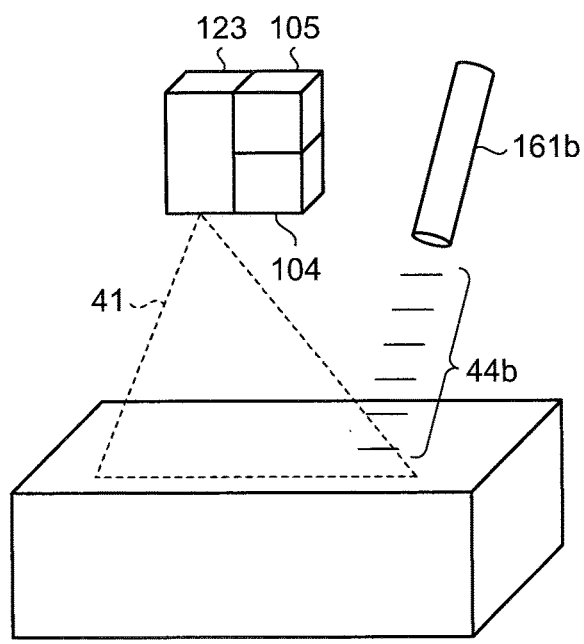
FIG. 52 is a schematic diagram illustrating the external force application process by the external force applying unit illustrated in FIG. 49.
Figure 53:
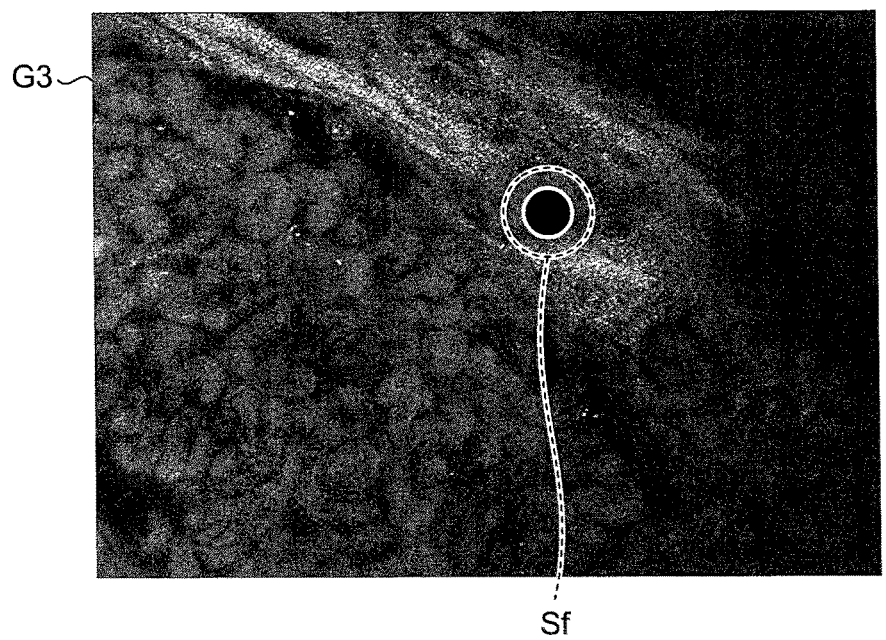
FIG. 53 is an example of the image which is displayed and output by the display device illustrated in FIG. 49.

FIGS. 50 and 52 are diagrams illustrating an external force application process by the external force applying unit 160 illustrated in FIG. 49. FIGS. 51 and 53 are examples of an image which is displayed and output by a display device 190. As illustrated in FIG. 50, for example, the external force applying unit 160 may output an air pulse 44a from a distal end 161a of the transmission path 161 (refer to FIG. 49) to a relatively wide area in the illumination area 42 of light output from an illumination optical system 123. As illustrated in FIG. 51, an image G2 which includes a striped line representing a variation in the hardness which is superimposed on a relatively wide area Sg in a normal image can be obtained by continuously performing a light emission process by the light source unit 121 and an imaging process for capturing a scattered signal which is formed by the imaging optical system 104 by the image sensor 105 with the output timing of the air pulse 44a to sequentially acquire interference components. Further, as illustrated in FIG. 52, when the external force applying unit 160 outputs a focused air pulse 44b from the distal end 161b of the transmission path 161 so that external force can be applied to a focused spot of the illumination area 42, it is possible to obtain an image G3 which represents a state of a variation in the hardness of a lesion in a focused spot Sf as illustrated in FIG. 53.

In this manner, in the fourth embodiment, the variation amount of the body tissue 100 can be continuously detected by continuously acquiring the interference component distribution by continuously performing a light emission process by the light source unit 121 and an imaging process for capturing a scattered signal formed by the imaging optical system 104 by the image sensor 105 while applying external force to the body tissue 100. Further, based on a result thereof, the characteristic value calculation unit 154 can also calculate the elasticity, the viscoelasticity, and the hardness of the body tissue 100. Although an example applied to the first embodiment has been described as the fourth embodiment, application to the second and third embodiments can, of course, be made.

Fifth Embodiment

Figure 54:
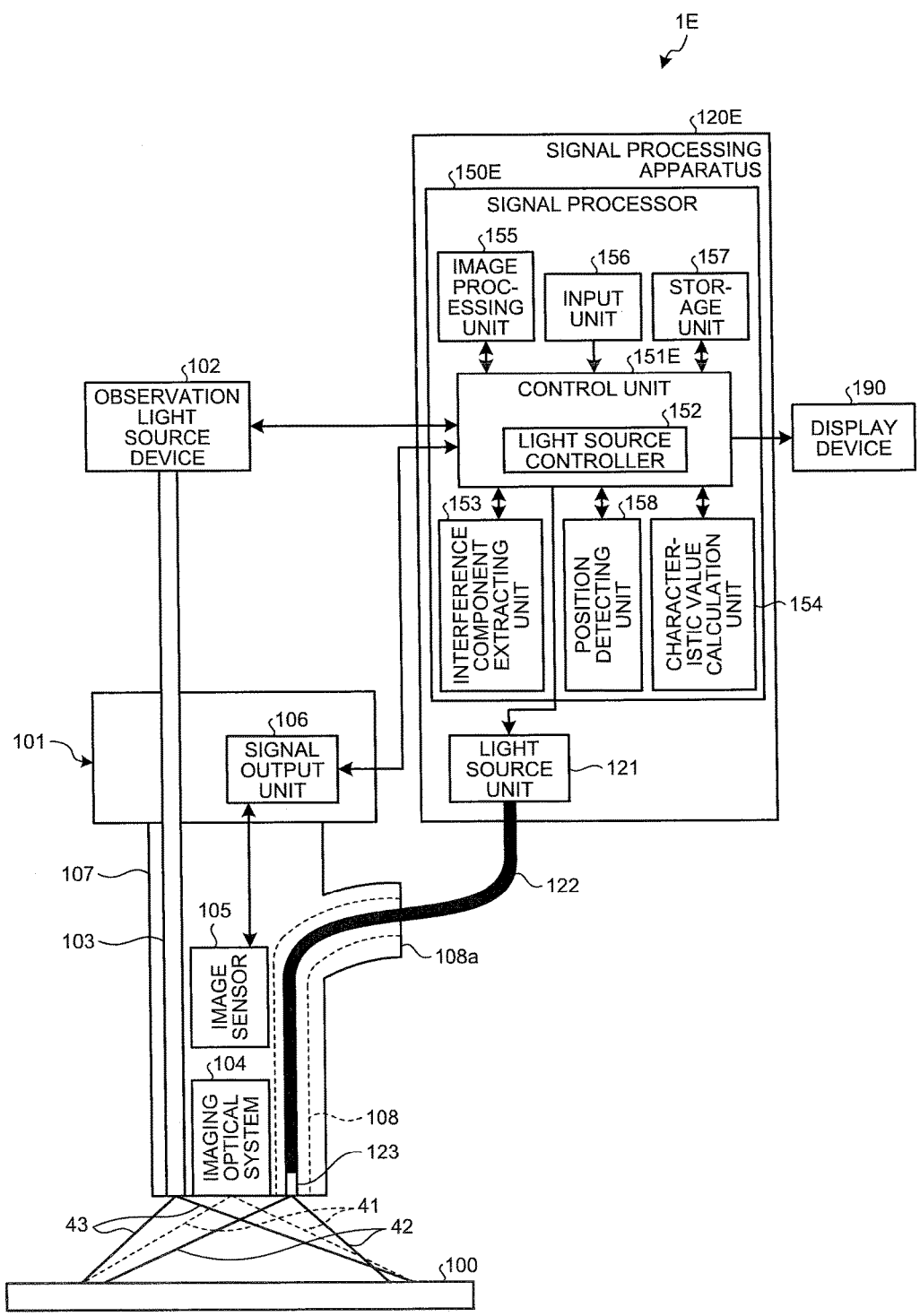
FIG. 54 is a diagram illustrating a schematic configuration of an endoscope system according to a fifth embodiment of the present invention.

Next, a fifth embodiment will be described. FIG. 54 is a diagram illustrating a schematic configuration of an endoscope system according to the fifth embodiment of the present invention.

As illustrated in FIG. 54, an endoscope system 1E according to the fifth embodiment includes a control unit 151E which has a function similar to the function of the control unit 151 and includes a signal processing apparatus 120E which is further provided with a position detecting unit 158 in a signal processor 150E as compared with the endoscope system 1 illustrated in FIG. 1.

The position detecting unit 158, for example, acquires the distance between spot-like interference component signal spots which are extracted when multi-spot lighting is performed by a light source unit 121. Then, the position detecting unit 158 detects a spatial positional relationship between a body tissue 100 which is a subject and an illumination point by comparing a previously obtained distance between spot-like interference component signal spots when a body tissue and an illumination optical system are separated by a known distance with each acquired distance. Further, also when single spot lighting is performed by the light source unit 121, the position detecting unit 158 is also capable of detecting the spatial positional relationship between the body tissue 100 and the illumination point by comparing a size and a deviation from a center pixel of an area where an interference component signal can be acquired with a size and a deviation from a center pixel of an interference signal area during spot lighting when the body tissue and the illumination optical system are separated by a known distance.

In this manner, in the endoscope system 1E, the generation of an interference component is limited within an area corresponding to an intensity of 10% of the maximum intensity of scattered and returned light from the center point of a focused illumination area. Thus, the detected interference component signal can also be used for accurate position detection with respect to a subject in which a luminous point is disadvantageously expanded by scattering. Further, the coherence length of partially coherent light emitted from the light source unit 121 may be adjusted to a coherence length in which an area within which the generation of an interference component is limited may be limited to, for example, 20% or 30% of the maximum intensity of scattered and returned light from the center point of illumination to increase the accuracy of position detection. Although an example applied to the first embodiment has been described as the fifth embodiment, application to the second to fourth embodiments can, of course, be made.

Sixth Embodiment

Figure 55:
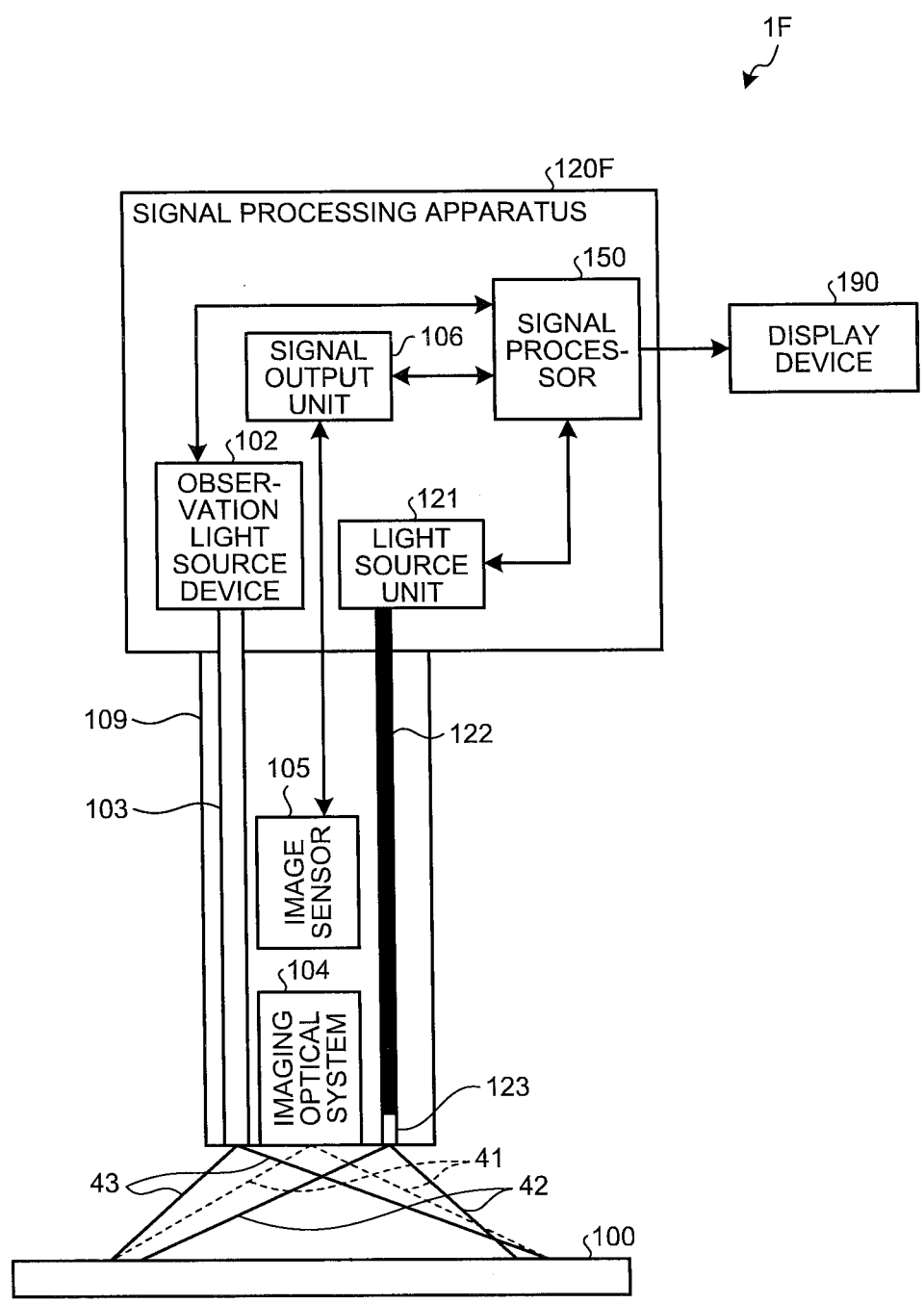
FIG. 55 is a diagram illustrating a schematic configuration of an endoscope system according to a sixth embodiment of the present invention.

Next, a sixth embodiment will be described. FIG. 55 is a diagram illustrating a schematic configuration of an endoscope system according to the sixth embodiment of the present invention.

As illustrated in FIG. 55, in an endoscope system 1F according to the sixth embodiment, a signal processing apparatus 120F is provided with an observation light source device 102, a signal output unit 106, and a casing 109 which is introduced into a subject. In the present invention, in addition to the configurations of the first to fifth embodiments in which the endoscope apparatus 101 and the signal processing apparatus 120 are separate bodies, a configuration in which a normal observation function and an interference component signal acquisition function are integrated can also be employed as with the sixth embodiment.

Figure 56:
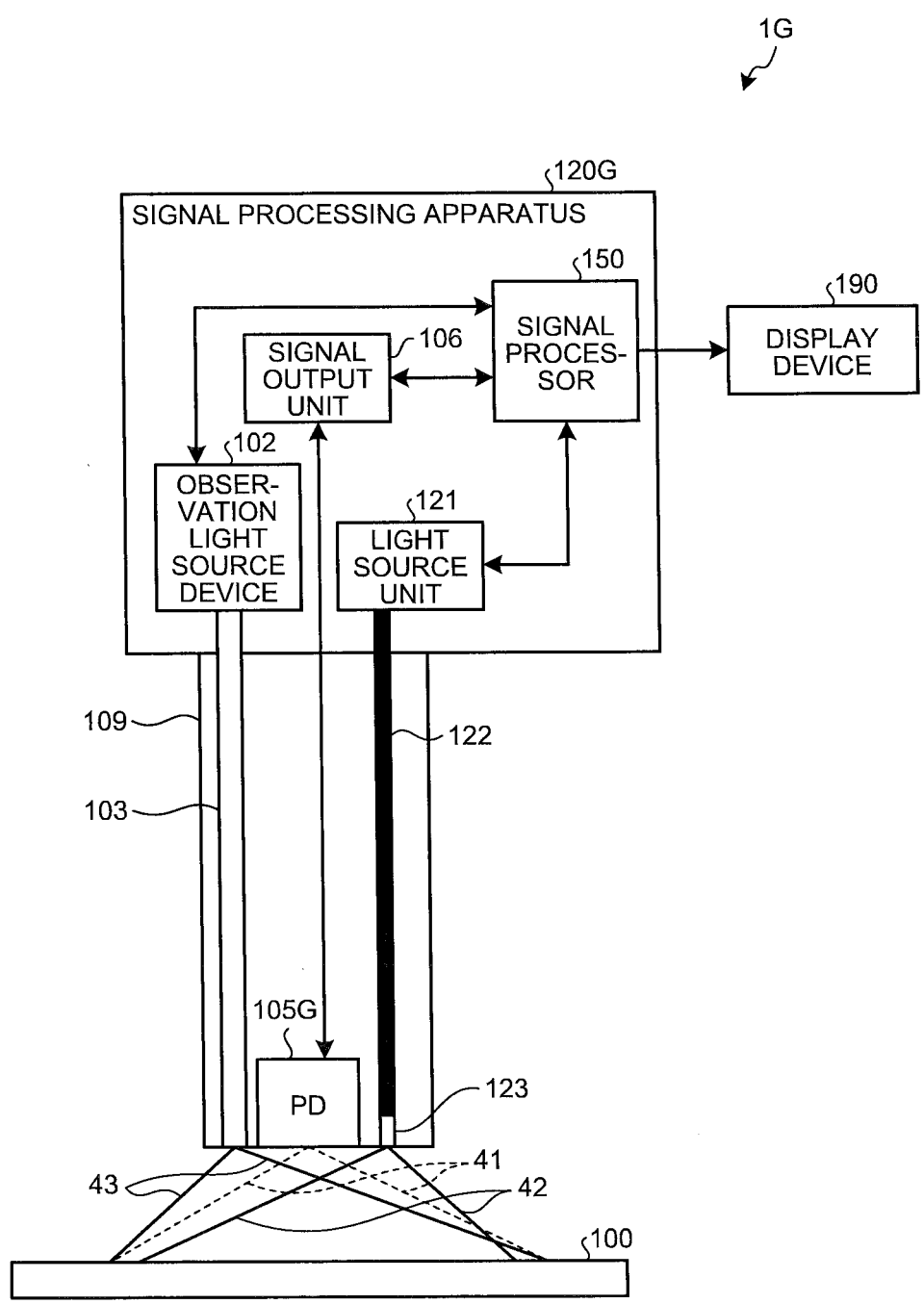
FIG. 56 is a diagram illustrating another example of the schematic configuration of the endoscope system according to the sixth embodiment.

FIG. 56 is a diagram illustrating another example of the schematic configuration of the endoscope system according to the sixth embodiment. As with an endoscope system 1G illustrated in FIG. 56, a signal processing apparatus 120G may include a photo detector (PD) 105G which is a planar photoelectric converter for performing photoelectric conversion on received light, instead of the image sensor 105 including a CMOS image sensor or a CCD image sensor. In this case, the imaging optical system 104 may be eliminated. When the PD 105G is employed, although separation in spatial intensity of an interference signal cannot be performed, an interference signal corresponding to movement of the surface layer of the body tissue 100 can be acquired by temporally continuously acquiring signals and separating a component that temporally varies (AC component) from a component that does not vary (DC component) to extract the AC component. Further, in this configuration, it is desired to apply a single spot light beam E1 (refer to FIG. 28) as illumination light for interference component extraction. Further, in order to improve the accuracy of a detection point, the light source unit 121 may adjust the coherence length of partially coherent light to be emitted to a coherence length in which an area within which the generation of an interference component is limited is limited to an area corresponding to more than 10% of the maximum intensity of scattered and returned light from the center point of the focused illumination area, for example, corresponding to the intensity of 20% or 30% thereof.

Further, the endoscope systems 1, and 1B to 1G according to the first to sixth embodiments can be applied not only to medical apparatuses such as a flexible endoscope, a rigid endoscope, and an operation microscope, but also to endoscope apparatuses which are industrially used. Further, the present invention can also be applied to microscope apparatuses.

FIG. 57 is a diagram illustrating a configuration when the first embodiment is applied to a microscope system. In FIG. 57, a plane on which a microscope system 2000 is placed is defined as an XY plane, and a direction perpendicular to the XY plane is defined as a Z direction for description. The microscope system 2000 illustrated in FIG. 57 is provided with a microscope apparatus 202 which observes a specimen SP, an imaging apparatus 203 which captures an image of the specimen SP through the microscope apparatus 202 and generates image data of the specimen SP, a signal processor 150, and a display device 190. The microscope apparatus 202, the imaging apparatus 203, and the signal processor 150 are connected by wire or wireless so that data can be transmitted and received.

The microscope apparatus 202 is provided with a body 200 having a substantially C shape, a stage 201 on which the specimen SP is placed, objective lenses 204a which include a plurality of objective lenses which are disposed facing the stage 201 and have different magnifications, a revolver 204b which holds the objective lenses 204a having different magnifications, a focusing unit 204c which moves the stage 201 in a perpendicular direction (Z-axis direction) which is perpendicular to a placement surface on which the specimen SP is placed to adjust the distance between the stage 201 and the objective lenses 204a, a focusing operation unit 205 which moves the focusing unit 204c up and down, a light source unit 121 which applies partially coherent light and weak coherent light to the specimen SP, an illumination optical system 206 which includes a plurality of optical systems, a trinocular tube unit 207 which is attached to the body 200, an eyepiece unit 208 which is attached through the trinocular tube unit 207, and a tube lens unit 209 which is coupled to the trinocular tube unit 207. Further, the imaging apparatus 203 which is provided with an image sensor 105 and a signal output unit 106 is connected to an end of the tube lens unit 209. The stage 201 is freely movable in the horizontal direction within the XY plane, and attached to the body 200 through the focusing unit 204c. Further, although not illustrated in FIG. 57, an epi-illumination light source for normal observation is also provided.

Also in this case, the light source unit 121 emits partially coherent light and weak coherent light to irradiate the specimen SP under control of the light source controller 152, and the interference component extracting unit 153 processes an image signal of the surface of the specimen SP which is captured by the image sensor 105 and extracts an interference component by excluding a noninterference component from the signal of scattered and returned light. The light source unit 121 emits a single spot light beam E1 or a plurality of spot light beams E2.

Further, an execution program for each processing executed in the signal processing apparatuses 120 and 120B to 120G according to the first to sixth embodiments and another configuration unit may be configured to be recorded in a computer-readable recording medium such as a CD-ROM, a flexible disk, a CD-R, or a DVD, as a file in an installable format or an executable format and provided, or may be configured to be stored on a computer connected to a network such as the Internet and provided by being downloaded through the network. Further, the execution program may be provided or distributed through a network such as the Internet.

According to some embodiments, a processing apparatus includes: a light source unit configured to emit partially coherent light having a coherence length that is equal to or more than inverse of a scattering coefficient of a light scattering body and shorter than half of inverse of a reduced scattering coefficient of the light scattering body; an illumination unit configured to irradiate an illumination area on a surface of the light scattering body, with the partially coherent light emitted from the light source unit; a detection unit configured to detect, in a detection area including the illumination area, a signal of scattered and returned light from the light scattering body; and an interference component extracting unit configured to extract an interference component by excluding a noninterference component from the signal of the scattered and returned light detected by the detection unit. With this feature, it is possible to accurately acquire only an interference component based on the scattered and returned light having been scattered and returned from a surface layer of the light scattering body.

Further, according to some embodiments, a processing apparatus includes: a light source unit configured to emit partially coherent light having a predefined coherence length for a scattering body of the same kind as a light scattering body, the predefined coherence length being defined to generate an interference component within an area showing an intensity of 10% of a maximum intensity of scattered and returned light from a center point of a focused illumination area on the scattering body, among an intensity distribution of internally scattered and returned light that is formed on a surface of the scattering body when focused illumination is performed on the scattering body; an illumination unit configured to irradiate an illumination area on a surface of the light scattering body, with the partially coherent light emitted from the light source unit; a detection unit configured to detect, in a detection area including the illumination area, a signal of scattered and returned light from the light scattering body; and an interference component extracting unit configured to extract an interference component by excluding a noninterference component from the signal of the scattered and returned light detected by the detection unit. With this feature, it is possible to accurately acquire only an interference component based on the scattered and returned light having been scattered and returned from a surface layer of the light scattering body.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A processing apparatus comprising:
a light source configured to emit:
partially coherent light having a coherence length that is equal to or more than inverse of a scattering coefficient of a light scattering body and shorter than half of inverse of a reduced scattering coefficient of the light scattering body; and
weak coherent light having a coherence length smaller than that of the partially coherent light;
an illumination optical system configured to irradiate an illumination area on a surface of the light scattering body, with the partially coherent light and the weak coherent light emitted from the light source;
a detector configured to detect, in a detection area including the illumination area, a first signal of scattered and returned light corresponding to the partially coherent light and a second signal of scattered and returned light corresponding to the weak coherent light, from the light scattering body; and
a processor comprising hardware, wherein the processor is configured to extract an interference component by excluding a noninterference component based on the second signal of the scattered and returned light corresponding to the weak coherent light from the first signal of the scattered and returned light corresponding to the partially coherent light.

2. A processing apparatus comprising:
a light source configured to emit:
partially coherent light having a predefined coherence length for a scattering body of the same kind as a light scattering body, the predefined coherence length being defined to generate an interference component within an area showing an intensity of 10% of a maximum intensity of scattered and returned light from a center point of a focused illumination area on the scattering body, among an intensity distribution of internally scattered and returned light that is formed on a surface of the scattering body when focused illumination is performed on the scattering body; and
weak coherent light having a coherence length smaller than that of the partially coherent light;
an illumination optical system configured to irradiate a two-dimensional illumination area on a surface of the light scattering body, with the partially coherent light and the weak coherent light emitted from the light source;
a detector configured to two-dimensionally detect, in a two-dimensional detection area including the two-dimensional illumination area, a first signal of scattered and returned light corresponding to the partially coherent light and a second signal of scattered and returned light corresponding to the weak coherent light, from the light scattering body; and a processor comprising hardware, wherein the processor is configured to extract an interference component by excluding a noninterference component based on the second signal of the scattered and returned light corresponding to the weak coherent light from the first signal of the scattered and returned light corresponding to the partially coherent light.

3. A processing apparatus comprising:
a light source configured to emit:
  partially coherent light having a coherence length that is equal to or more than inverse of a scattering coefficient of a light scattering body and shorter than half of inverse of a reduced scattering coefficient of the light scattering body, the coherence length being a predefined coherence length for a scattering body of the same kind as the light scattering body, the predefined coherence length being defined to generate an interference component within an area showing an intensity of 10% of a maximum intensity of scattered and returned light from a center point of a focused illumination area on the scattering body, among an intensity distribution of internally scattered and returned light that is formed on a surface of the scattering body when focused illumination is performed on the scattering body; and
  weak coherent light having a coherence length smaller than that of the partially coherent light;
an illumination optical system configured to irradiate an illumination area on a surface of the light scattering body, with the partially coherent light and the weak coherent light emitted from the light source;
a detector configured to detect, in a detection area including the illumination area, a first signal of scattered and returned light corresponding to the partially coherent light and a second signal of scattered and returned light corresponding to the weak coherent light, from the light scattering body; and
a processor comprising hardware, wherein the processor is configured to extract an interference component by excluding a noninterference component based on the second signal of the scattered and returned light corresponding to the weak coherent light from the first signal of the scattered and returned light corresponding to the partially coherent light.

4. The processing apparatus according to claim 1,
wherein the processor is configured to extract the interference component by calculating a difference between an intensity of the scattered and returned light corresponding to the partially coherent light based on the first signal and an intensity of the scattered and returned light corresponding to the weak coherent light based on the second signal.

5. The processing apparatus according to claim 4,
wherein the processor is configured to:
  control the light source to emit the partially coherent light and the weak coherent light at different points in time, and
  calculate the difference between the intensity of the scattered and returned light detected by the detector at time of emitting the partially coherent light based on the first signal and the intensity of the scattered and returned light detected by the detector at time of emitting the weak coherent light based on the second signal.

6. The processing apparatus according to claim 5,
wherein the light source is configured to emit the partially coherent light and the weak coherent light such that a wavelength band of a full width at half maximum of one of the partially coherent light and the weak coherent light overlaps at least a center wavelength of the other of the partially coherent light and the weak coherent light.

7. The processing apparatus according to claim 5,
wherein the light source is configured to emit broadband light including at least a wavelength band of the partially coherent light and a wavelength band of the weak coherent light,
wherein the processing apparatus comprises:
  a first filter configured to pass light having the wavelength band of the partially coherent light of the broadband light emitted by the light source;
  a second filter configured to pass light having the wavelength band of the weak coherent light of the broadband light emitted by the light source; and
  an actuator configured to move one of the first filter and the second filter onto an optical path of the light source, and
wherein the processor is configured to control the actuator to move the first filter onto the optical path of the light source at the time of emitting the partially coherent light and move the second filter onto the optical path of the light source at the time of emitting the weak coherent light.

8. The processing apparatus according to claim 5,
wherein the light source comprises:
  a first light source configured to emit the partially coherent light; and
  a second light source configured to emit the weak coherent light, and
  wherein the processor is configured to control the first light source to emit the partially coherent light at the time of emitting the partially coherent light and control the second light source to emit the weak coherent light at the time of emitting the weak coherent light.

9. The processing apparatus according to claim 4,
wherein the light source is configured to synchronously emit the partially coherent light and the weak coherent light having a wavelength band of a full width at half maximum that does not overlap a wavelength band of a full width at half maximum of the partially coherent light, and
wherein the processing apparatus further comprises a filter group disposed at an input stage of the detector, wherein the filter group is configured to disperse light into wavelength band light corresponding to the partially coherent light and wavelength band light corresponding to the weak coherent light.

10. The processing apparatus according to claim 9,
wherein the filter group is configured to disperse the light into the partially coherent light and the weak coherent light such that an integrated intensity of the partially coherent light and an integrated intensity of the weak coherent light at time of emission in the light source are equal to each other.

11. The processing apparatus according to claim 4, further comprising a beam profile shaping optical system configured to cause emitted light spatial distributions of the partially coherent light and the weak coherent light input to the illumination optical system, to be equal to each other.

12. The processing apparatus according to claim 1,
wherein the detector comprises an image sensor comprising a plurality of pixels arranged in a matrix form, the plurality of pixels being configured to receive light and perform photoelectric conversion on the received light to generate an image signal.

13. The processing apparatus according to claim 1, wherein the detector is a planar photoelectric converter configured to receive light and perform photoelectric conversion on the received light.

14. The processing apparatus according to claim 1, further comprising an actuator configured to apply external force that contactlessly deforms the surface of the light scattering body.

* * * * *